(12) United States Patent
Chaplin et al.

(10) Patent No.: US 9,463,238 B2
(45) Date of Patent: Oct. 11, 2016

(54) RECOMBINANT POXVIRUS VECTOR COMPRISING TETANUS TOXIN FRAGMENT C

(71) Applicant: Bavarian Nordic A/S, Kvistgaard (DK)

(72) Inventors: Paul Chaplin, Grafelfing (DE); Robin Steigerwald, Munich (DE)

(73) Assignee: BAVARIAN NORDIC A/S, Kvistgaard (DK)

( * ) Notice: Subject to any disclaimer, the term of this patent is extended or adjusted under 35 U.S.C. 154(b) by 72 days.

(21) Appl. No.: 14/363,287

(22) PCT Filed: Nov. 30, 2012

(86) PCT No.: PCT/EP2012/004949
§ 371 (c)(1),
(2) Date: Jun. 5, 2014

(87) PCT Pub. No.: WO2013/083254
PCT Pub. Date: Jun. 13, 2013

(65) Prior Publication Data
US 2014/0322265 A1    Oct. 30, 2014

Related U.S. Application Data

(60) Provisional application No. 61/568,857, filed on Dec. 9, 2011.

(51) Int. Cl.
*A61K 39/385* (2006.01)
*A61K 39/07* (2006.01)
*A61K 39/00* (2006.01)

(52) U.S. Cl.
CPC ............ *A61K 39/385* (2013.01); *A61K 39/07* (2013.01); *A61K 2039/5256* (2013.01); *A61K 2039/6037* (2013.01); *A61K 2039/70* (2013.01)

(58) Field of Classification Search
None
See application file for complete search history.

(56) References Cited

FOREIGN PATENT DOCUMENTS

| WO | WO 92/22641 A1 | 12/1992 |
|---|---|---|
| WO | WO 2008/045346 A2 | 4/2008 |
| WO | WO 2010/054156 A2 | 5/2010 |
| WO | WO 2010/134094 A1 * | 11/2010 |

OTHER PUBLICATIONS

Williamson and Dyson, Frontiers in Microbiology, Sep. 24, 2015, vol. 5, Article 1009, eight pages.*
Fairweather and Lyness, Nucleic Acids Research, 1986, 14(19):7809-7812.*
Aminian et al., Expression and purification of a trivalent pertussis toxin-diphtheria toxin-tetanus toxin fusion protein in *Escherichia coli*, Protein Expression & Purification, Aug. 1, 2006, 170-178, vol. 51.
Dong et al., Assessment of a vaccinia virus vectored multi-epitope live vaccine candidate fro *Plasmodium falciparum*, International Journal for Parasitology, 2001, 57-62, vol. 31.
Embry et al., Enhancement of immune response to an antigen delivered by vaccinia virus by displaying the antigen on the surface of intracellular mature virion, Vaccine, Jun. 12, 2011, 5331-5339, vol. 29.
Merkel et al., Development of a highly efficacious vaccinia-based duel vaccine against smallpox and anthrax, two important bioterror entities, PNAS, Oct. 19, 2010, 18091-18096, vol. 107.
Mesnage et al., Cell Surface-Exposed tetanus toxin Fragment C Produced by Recombinant *Bacillus anthracis* protects against Tetanus Toxin, Infection and Immunity, Sep. 1999, 4847-4850, vol. 67.
European Patent Office Communication enclosing Extended European Search Report for EP Application 11009722.7, dated May 15, 2012.
International Search report for PCT/EP2012/004949, dated Mar. 5, 2013.
Written Opinion of the International Search Authority for PCT/EP2012/004949, dated Mar. 5, 2013.

* cited by examiner

*Primary Examiner* — Stacy B Chen

(57) ABSTRACT

The present invention relates to a recombinant poxvirus comprising tetanus toxin fragment C for improved immunogenicity of an antigen and related methods and uses. Specifically, the present invention generally relates to genetically engineered (recombinant) poxvirus vectors comprising a tetanus toxin fragment C (TTC) coding sequence operably linked to a bacterial antigenic determinant as well as to uses thereof, e.g., to affect an immune response in a subject.

19 Claims, 4 Drawing Sheets

SEQUENCE LISTING

```
<160> NUMBER OF SEQ ID NOS: 12

<210> SEQ ID NO 1
<211> LENGTH: 3642
<212> TYPE: DNA
<213> ORGANISM: Artificial
<220> FEATURE:
<223> OTHER INFORMATION: construct SecTag2-PA83-TTC
<220> FEATURE:
<221> NAME/KEY: misc_feature
<222> LOCATION: (1)..(63)
<223> OTHER INFORMATION: SecTag2
<220> FEATURE:
<221> NAME/KEY: CDS
<222> LOCATION: (1)..(3642)
<220> FEATURE:
<221> NAME/KEY: misc_feature
<222> LOCATION: (64)..(2271)
<223> OTHER INFORMATION: PA83
<220> FEATURE:
<221> NAME/KEY: misc_feature
<222> LOCATION: (2281)..(3642)
<223> OTHER INFORMATION: TTC

<400> SEQUENCE: 1 atg gag acc gac acc ctg ctg ctg tgg gtc ctg ctc ctg tgg gtg ccc      48
Met Glu Thr Asp Thr Leu Leu Leu Trp Val Leu Leu Leu Trp Val Pro
1               5                   10                  15 ggc agc acc ggc gac gaa gtg aag cag gaa aac cgg ctg ctg aac gag      96
Gly Ser Thr Gly Asp Glu Val Lys Gln Glu Asn Arg Leu Leu Asn Glu
            20                  25                  30 agc gag agc agc agc cag ggc ctg ctg ggc tac tac ttc agc gac ctg     144
Ser Glu Ser Ser Ser Gln Gly Leu Leu Gly Tyr Tyr Phe Ser Asp Leu
        35                  40                  45 aac ttc cag gcc ccc atg gtg gtg acc agc agc acc acc ggc gac ctg     192
Asn Phe Gln Ala Pro Met Val Val Thr Ser Ser Thr Thr Gly Asp Leu
    50                  55                  60 agc atc ccc agc agc gag ctg gaa aac atc ccc agc gag aac cag tac     240
Ser Ile Pro Ser Ser Glu Leu Glu Asn Ile Pro Ser Glu Asn Gln Tyr
65                  70                  75                  80
```

```
ttc cag agc gcc att tgg agc ggc ttc atc aaa gtg aag aag tcc gac       288
Phe Gln Ser Ala Ile Trp Ser Gly Phe Ile Lys Val Lys Lys Ser Asp
                85                  90                  95 gag tac acc ttc gcc acc tcc gcc gac aac cac gtg acc atg tgg gtg       336
Glu Tyr Thr Phe Ala Thr Ser Ala Asp Asn His Val Thr Met Trp Val
            100                 105                 110 gac gac cag gaa gtg atc aac aag gcc agc aac agc aac aag atc cgg       384
Asp Asp Gln Glu Val Ile Asn Lys Ala Ser Asn Ser Asn Lys Ile Arg
        115                 120                 125 ctg gaa aag ggc cgg ctg tac cag atc aag atc cag tac cag aga gag       432
Leu Glu Lys Gly Arg Leu Tyr Gln Ile Lys Ile Gln Tyr Gln Arg Glu
    130                 135                 140 aac ccc acc gag aag ggc ctg gac ttc aag ctg tac tgg acc gac agc       480
Asn Pro Thr Glu Lys Gly Leu Asp Phe Lys Leu Tyr Trp Thr Asp Ser
145                 150                 155                 160 cag aac aag aaa gaa gtg atc agc agc gac aac ctg cag ctg ccc gag       528
Gln Asn Lys Lys Glu Val Ile Ser Ser Asp Asn Leu Gln Leu Pro Glu
                165                 170                 175 ctg aag cag aag tcc agc aac tcc cgg aag aag cgg agc acc agc gcc       576
Leu Lys Gln Lys Ser Ser Asn Ser Arg Lys Lys Arg Ser Thr Ser Ala
            180                 185                 190 gga ccc acc gtg ccc gac cgg gac aac gac ggc atc ccc gac agc ctg       624
Gly Pro Thr Val Pro Asp Arg Asp Asn Asp Gly Ile Pro Asp Ser Leu
        195                 200                 205 gaa gtg gag ggc tac acc gtg gac gtg aag aac aag cgg acc ttc ctg       672
Glu Val Glu Gly Tyr Thr Val Asp Val Lys Asn Lys Arg Thr Phe Leu
    210                 215                 220 agc ccc tgg atc agc aac atc cac gag aag aag ggg ctg acc aag tac       720
Ser Pro Trp Ile Ser Asn Ile His Glu Lys Lys Gly Leu Thr Lys Tyr
225                 230                 235                 240 aag agc agc ccc gag aag tgg agc acc gcc agc gac ccc tac agc gac       768
Lys Ser Ser Pro Glu Lys Trp Ser Thr Ala Ser Asp Pro Tyr Ser Asp
                245                 250                 255 ttc gag aaa gtg acc ggc cgg atc gac aag aac gtg tcc ccc gag gcc       816
Phe Glu Lys Val Thr Gly Arg Ile Asp Lys Asn Val Ser Pro Glu Ala
            260                 265                 270 aga cac cct ctg gtg gcc gcc tac ccc atc gtg cac gtg gac atg gaa       864
Arg His Pro Leu Val Ala Ala Tyr Pro Ile Val His Val Asp Met Glu
        275                 280                 285 aat atc atc ctg agc aag aac gag gac cag agc acc cag aac acc gac       912
Asn Ile Ile Leu Ser Lys Asn Glu Asp Gln Ser Thr Gln Asn Thr Asp
    290                 295                 300 tcc cag acc cgg acc atc agc aag aac acc agc acc agc aga acc cac       960
Ser Gln Thr Arg Thr Ile Ser Lys Asn Thr Ser Thr Ser Arg Thr His
305                 310                 315                 320 aca agc gaa gtg cac ggc aac gcc gaa gtg cac gcc agc ttt ttc gac      1008
Thr Ser Glu Val His Gly Asn Ala Glu Val His Ala Ser Phe Phe Asp
                325                 330                 335 atc gga ggg agc gtg tcc gcc ggc ttc agc aac tcc aac agc agc acc      1056
Ile Gly Gly Ser Val Ser Ala Gly Phe Ser Asn Ser Asn Ser Ser Thr
            340                 345                 350 gtg gcc atc gac cac agc ctg agc ctg gcc ggc gag aga acc tgg gcc      1104
Val Ala Ile Asp His Ser Leu Ser Leu Ala Gly Glu Arg Thr Trp Ala
        355                 360                 365 gag aca atg ggc ctg aac acc gcc gac acc gcc aga ctg aac gcc aac      1152
Glu Thr Met Gly Leu Asn Thr Ala Asp Thr Ala Arg Leu Asn Ala Asn
    370                 375                 380 atc cgc tac gtg aac acc ggc acc gcc ccc atc tac aac gtg ctg ccc      1200
Ile Arg Tyr Val Asn Thr Gly Thr Ala Pro Ile Tyr Asn Val Leu Pro
385                 390                 395                 400
```

```
acc acc tcc ctg gtg ctg ggc aag aac cag acc ctg gcc acc atc aag     1248
Thr Thr Ser Leu Val Leu Gly Lys Asn Gln Thr Leu Ala Thr Ile Lys
            405                 410                 415 gcc aaa gag aac cag ctg tcc cag atc ctg gcc ccc aac aac tac tac     1296
Ala Lys Glu Asn Gln Leu Ser Gln Ile Leu Ala Pro Asn Asn Tyr Tyr
        420                 425                 430 ccc agc aag aac ctg gcc cct atc gcc ctg aac gcc cag gac gac ttc     1344
Pro Ser Lys Asn Leu Ala Pro Ile Ala Leu Asn Ala Gln Asp Asp Phe
        435                 440                 445 tct tct acc ccc atc acc atg aac tac aac cag ttt ctg gaa ctg gaa     1392
Ser Ser Thr Pro Ile Thr Met Asn Tyr Asn Gln Phe Leu Glu Leu Glu
        450                 455                 460 aag acc aag cag ctg cgg ctg gac acc gac cag gtg tac ggc aat atc     1440
Lys Thr Lys Gln Leu Arg Leu Asp Thr Asp Gln Val Tyr Gly Asn Ile
465                 470                 475                 480 gcc acc tac aac ttc gag aac ggc aga gtg cgc gtg gac acc ggc agc     1488
Ala Thr Tyr Asn Phe Glu Asn Gly Arg Val Arg Val Asp Thr Gly Ser
                485                 490                 495 aat tgg agc gag gtg ctg cct cag atc cag gaa acc acc gcc cgg atc     1536
Asn Trp Ser Glu Val Leu Pro Gln Ile Gln Glu Thr Thr Ala Arg Ile
            500                 505                 510 atc ttc aac ggc aag gac ctg aac ctg gtg gag cgg cgg atc gcc gcc     1584
Ile Phe Asn Gly Lys Asp Leu Asn Leu Val Glu Arg Arg Ile Ala Ala
        515                 520                 525 gtg aac ccc tcc gac ccc ctg gaa acc acc aag ccc gac atg acc ctg     1632
Val Asn Pro Ser Asp Pro Leu Glu Thr Thr Lys Pro Asp Met Thr Leu
        530                 535                 540 aaa gag gcc ctg aag atc gcc ttc ggc ttc aac gag ccc aac ggc aac     1680
Lys Glu Ala Leu Lys Ile Ala Phe Gly Phe Asn Glu Pro Asn Gly Asn
545                 550                 555                 560 ctg cag tac cag ggc aag gac atc acc gag ttc gac ttc aac ttc gac     1728
Leu Gln Tyr Gln Gly Lys Asp Ile Thr Glu Phe Asp Phe Asn Phe Asp
                565                 570                 575 cag cag acc tcc cag aac atc aag aat cag ctg gcc gaa ctg aac gtg     1776
Gln Gln Thr Ser Gln Asn Ile Lys Asn Gln Leu Ala Glu Leu Asn Val
            580                 585                 590 acc aac atc tac aca gtg ctg gac aag atc aag ctg aat gcc aag atg     1824
Thr Asn Ile Tyr Thr Val Leu Asp Lys Ile Lys Leu Asn Ala Lys Met
        595                 600                 605 aac atc ctg atc cgg gac aag cgg ttc cac tac gac cgg aac aat atc     1872
Asn Ile Leu Ile Arg Asp Lys Arg Phe His Tyr Asp Arg Asn Asn Ile
        610                 615                 620 gcc gtg ggc gcc gac gag agc gtg gtg aaa gaa gcc cac cgg gaa gtc     1920
Ala Val Gly Ala Asp Glu Ser Val Val Lys Glu Ala His Arg Glu Val
625                 630                 635                 640 att aac agc tcc acc gag ggg ctg ctg ctg aac atc gac aag gac atc     1968
Ile Asn Ser Ser Thr Glu Gly Leu Leu Leu Asn Ile Asp Lys Asp Ile
                645                 650                 655 cgc aag atc ctg agc ggc tac atc gtg gag atc gag gac acc gag ggc     2016
Arg Lys Ile Leu Ser Gly Tyr Ile Val Glu Ile Glu Asp Thr Glu Gly
            660                 665                 670 ctg aaa gaa gtc att aac gac cgc tac gac atg ctg aat atc agc agc     2064
Leu Lys Glu Val Ile Asn Asp Arg Tyr Asp Met Leu Asn Ile Ser Ser
        675                 680                 685 ctg cgg cag gac ggc aag acc ttc atc gac ttc aag aag tac aac gac     2112
Leu Arg Gln Asp Gly Lys Thr Phe Ile Asp Phe Lys Lys Tyr Asn Asp
        690                 695                 700 aag ctg ccc ctg tac atc agc aac ccc aac tac aaa gtg aac gtg tac     2160
Lys Leu Pro Leu Tyr Ile Ser Asn Pro Asn Tyr Lys Val Asn Val Tyr
705                 710                 715                 720
```

```
gcc gtg acc aaa gag aat acc atc atc aac cct agc gag aac ggc gac    2208
Ala Val Thr Lys Glu Asn Thr Ile Ile Asn Pro Ser Glu Asn Gly Asp
            725                 730                 735 acc tcc acc aac ggc atc aag aag atc ctg atc ttc agc aag aag ggc    2256
Thr Ser Thr Asn Gly Ile Lys Lys Ile Leu Ile Phe Ser Lys Lys Gly
            740                 745                 750 tac gag atc ggc gga ccc ggc cct aag aac ctg gac tgc tgg gtg gac    2304
Tyr Glu Ile Gly Gly Pro Gly Pro Lys Asn Leu Asp Cys Trp Val Asp
            755                 760                 765 aac gaa gag gac atc gac gtg atc ctg aag aag tct acc atc ctg aat    2352
Asn Glu Glu Asp Ile Asp Val Ile Leu Lys Lys Ser Thr Ile Leu Asn
            770                 775                 780 ctg gac atc aac aac gac atc atc agc gac atc tcc ggc ttc aac agc    2400
Leu Asp Ile Asn Asn Asp Ile Ile Ser Asp Ile Ser Gly Phe Asn Ser
785                 790                 795                 800 agc gtg atc acc tac ccc gac gcc cag ctg gtg cct ggc atc aat ggc    2448
Ser Val Ile Thr Tyr Pro Asp Ala Gln Leu Val Pro Gly Ile Asn Gly
            805                 810                 815 aag gcc atc cac ctg gtg aac aac gag agc agc gaa gtg atc gtg cac    2496
Lys Ala Ile His Leu Val Asn Asn Glu Ser Ser Glu Val Ile Val His
            820                 825                 830 aag gcc atg gac atc gag tac aac gat atg ttc aac aac ttc acc gtg    2544
Lys Ala Met Asp Ile Glu Tyr Asn Asp Met Phe Asn Asn Phe Thr Val
            835                 840                 845 tcc ttt tgg ctg cgg gtg ccc aag gtg tcc gcc agc cac ctg gaa cag    2592
Ser Phe Trp Leu Arg Val Pro Lys Val Ser Ala Ser His Leu Glu Gln
            850                 855                 860 tac ggc acc aac gag tac agc atc atc agc agc atg aag aag cac agc    2640
Tyr Gly Thr Asn Glu Tyr Ser Ile Ile Ser Ser Met Lys Lys His Ser
865                 870                 875                 880 ctg tcc atc ggc agc ggg tgg agc gtg tcc ctg aag ggc aac aac ctg    2688
Leu Ser Ile Gly Ser Gly Trp Ser Val Ser Leu Lys Gly Asn Asn Leu
            885                 890                 895 atc tgg acc ctg aag gac tct gcc ggc gaa gtg cgg cag atc acc ttc    2736
Ile Trp Thr Leu Lys Asp Ser Ala Gly Glu Val Arg Gln Ile Thr Phe
            900                 905                 910 cgc gac ctg ccc gac aag ttc aac gcc tac ctg gcc aat aag tgg gtg    2784
Arg Asp Leu Pro Asp Lys Phe Asn Ala Tyr Leu Ala Asn Lys Trp Val
            915                 920                 925 ttc atc acc atc acc aac gac aga ctg tcc agc gcc aac ctg tat atc    2832
Phe Ile Thr Ile Thr Asn Asp Arg Leu Ser Ser Ala Asn Leu Tyr Ile
            930                 935                 940 aac ggc gtg ctg atg ggc agc gcc gag atc aca ggc ctg ggc gcc atc    2880
Asn Gly Val Leu Met Gly Ser Ala Glu Ile Thr Gly Leu Gly Ala Ile
945                 950                 955                 960 cgg gag gac aac aac atc acc ctg aag ctg gac cgg tgc aac aac aac    2928
Arg Glu Asp Asn Asn Ile Thr Leu Lys Leu Asp Arg Cys Asn Asn Asn
            965                 970                 975 aac cag tac gtg tcc atc gac aag ttc cgc atc ttc tgc aag gcc ctg    2976
Asn Gln Tyr Val Ser Ile Asp Lys Phe Arg Ile Phe Cys Lys Ala Leu
            980                 985                 990 aat ccc aaa gag atc gag aag ctg  tac acc agc tac ctg  tcc atc acc   3024
Asn Pro Lys Glu Ile Glu Lys Leu  Tyr Thr Ser Tyr Leu  Ser Ile Thr
            995                  1000                 1005 ttt ctg  cgg gat ttc tgg ggc  aac cct ctg aga tac  gac acc gag       3069
Phe Leu  Arg Asp Phe Trp Gly  Asn Pro Leu Arg Tyr  Asp Thr Glu
         1010                 1015                 1020 tac tac  ctg atc ccc gtg gcc  agc agc tcc aag gac  gtg cag ctg       3114
Tyr Tyr  Leu Ile Pro Val Ala  Ser Ser Ser Lys Asp  Val Gln Leu
         1025                 1030                 1035
```

```
aag aac atc acc gac tac atg tac ctg acc aac gcc ccc agc tac      3159
Lys Asn Ile Thr Asp Tyr Met Tyr Leu Thr Asn Ala Pro Ser Tyr
    1040                1045                1050 acc aat ggc aag ctg aac atc tac tac cgg cgg ctg tac aac ggc      3204
Thr Asn Gly Lys Leu Asn Ile Tyr Tyr Arg Arg Leu Tyr Asn Gly
1055                1060                1065 ctg aag ttc atc atc aag cgg tac acc ccc aac aat gag atc gac      3249
Leu Lys Phe Ile Ile Lys Arg Tyr Thr Pro Asn Asn Glu Ile Asp
1070                1075                1080 agc ttc gtg aag tcc ggc gac ttc atc aag ctg tat gtg tcc tac      3294
Ser Phe Val Lys Ser Gly Asp Phe Ile Lys Leu Tyr Val Ser Tyr
    1085                1090                1095 aac aac aat gag cac atc gtg ggc tac ccc aag gac ggg aac gcc      3339
Asn Asn Asn Glu His Ile Val Gly Tyr Pro Lys Asp Gly Asn Ala
1100                1105                1110 ttc aac aac ctg gac cgg atc ctg aga gtg ggc tac aac gcc cct      3384
Phe Asn Asn Leu Asp Arg Ile Leu Arg Val Gly Tyr Asn Ala Pro
    1115                1120                1125 ggc atc ccc ctg tac aag aaa atg gaa gcc gtg aag ctg cgg gac      3429
Gly Ile Pro Leu Tyr Lys Lys Met Glu Ala Val Lys Leu Arg Asp
1130                1135                1140 ctg aaa acc tac tct gtg cag ctg aaa ctg tac gac gac aag aac      3474
Leu Lys Thr Tyr Ser Val Gln Leu Lys Leu Tyr Asp Asp Lys Asn
    1145                1150                1155 gcc agc ctg ggc ctg gtg ggg acc cac aac ggc cag atc ggc aac      3519
Ala Ser Leu Gly Leu Val Gly Thr His Asn Gly Gln Ile Gly Asn
1160                1165                1170 gac ccc aac cgg gat atc ctg atc gcc agc aac tgg tac ttc aac      3564
Asp Pro Asn Arg Asp Ile Leu Ile Ala Ser Asn Trp Tyr Phe Asn
    1175                1180                1185 cac ctg aag gac aag atc ctg ggc tgc gat tgg tac ttc gtg ccc      3609
His Leu Lys Asp Lys Ile Leu Gly Cys Asp Trp Tyr Phe Val Pro
1190                1195                1200 acc gac gag ggc tgg acc aac gac aag ctt tga                      3642
Thr Asp Glu Gly Trp Thr Asn Asp Lys Leu
    1205                1210
```

<210> SEQ ID NO 2
<211> LENGTH: 1213
<212> TYPE: PRT
<213> ORGANISM: Artificial
<220> FEATURE:
<223> OTHER INFORMATION: Synthetic Construct

<400> SEQUENCE: 2

```
Met Glu Thr Asp Thr Leu Leu Leu Trp Val Leu Leu Leu Trp Val Pro
1               5                   10                  15

Gly Ser Thr Gly Asp Glu Val Lys Gln Glu Asn Arg Leu Leu Asn Glu
            20                  25                  30

Ser Glu Ser Ser Ser Gln Gly Leu Leu Gly Tyr Tyr Phe Ser Asp Leu
        35                  40                  45

Asn Phe Gln Ala Pro Met Val Val Thr Ser Ser Thr Thr Gly Asp Leu
    50                  55                  60

Ser Ile Pro Ser Ser Glu Leu Glu Asn Ile Pro Ser Glu Asn Gln Tyr
65                  70                  75                  80

Phe Gln Ser Ala Ile Trp Ser Gly Phe Ile Lys Val Lys Lys Ser Asp
                85                  90                  95

Glu Tyr Thr Phe Ala Thr Ser Ala Asp Asn His Val Thr Met Trp Val
            100                 105                 110
```

```
Asp Asp Gln Glu Val Ile Asn Lys Ala Ser Asn Ser Asn Lys Ile Arg
            115                 120                 125

Leu Glu Lys Gly Arg Leu Tyr Gln Ile Lys Ile Gln Tyr Gln Arg Glu
        130                 135                 140

Asn Pro Thr Glu Lys Gly Leu Asp Phe Lys Leu Tyr Trp Thr Asp Ser
145                 150                 155                 160

Gln Asn Lys Lys Glu Val Ile Ser Ser Asp Asn Leu Gln Leu Pro Glu
                165                 170                 175

Leu Lys Gln Lys Ser Ser Asn Ser Arg Lys Lys Arg Ser Thr Ser Ala
            180                 185                 190

Gly Pro Thr Val Pro Asp Arg Asp Asn Asp Gly Ile Pro Asp Ser Leu
        195                 200                 205

Glu Val Glu Gly Tyr Thr Val Asp Val Lys Asn Lys Arg Thr Phe Leu
    210                 215                 220

Ser Pro Trp Ile Ser Asn Ile His Glu Lys Lys Gly Leu Thr Lys Tyr
225                 230                 235                 240

Lys Ser Ser Pro Glu Lys Trp Ser Thr Ala Ser Asp Pro Tyr Ser Asp
                245                 250                 255

Phe Glu Lys Val Thr Gly Arg Ile Asp Lys Asn Val Ser Pro Glu Ala
            260                 265                 270

Arg His Pro Leu Val Ala Ala Tyr Pro Ile Val His Val Asp Met Glu
        275                 280                 285

Asn Ile Ile Leu Ser Lys Asn Glu Asp Gln Ser Thr Gln Asn Thr Asp
    290                 295                 300

Ser Gln Thr Arg Thr Ile Ser Lys Asn Thr Ser Thr Ser Arg Thr His
305                 310                 315                 320

Thr Ser Glu Val His Gly Asn Ala Glu Val His Ala Ser Phe Phe Asp
                325                 330                 335

Ile Gly Gly Ser Val Ser Ala Gly Phe Ser Asn Ser Asn Ser Ser Thr
            340                 345                 350

Val Ala Ile Asp His Ser Leu Ser Leu Ala Gly Glu Arg Thr Trp Ala
        355                 360                 365

Glu Thr Met Gly Leu Asn Thr Ala Asp Thr Ala Arg Leu Asn Ala Asn
    370                 375                 380

Ile Arg Tyr Val Asn Thr Gly Thr Ala Pro Ile Tyr Asn Val Leu Pro
385                 390                 395                 400

Thr Thr Ser Leu Val Leu Gly Lys Asn Gln Thr Leu Ala Thr Ile Lys
                405                 410                 415

Ala Lys Glu Asn Gln Leu Ser Gln Ile Leu Ala Pro Asn Asn Tyr Tyr
            420                 425                 430

Pro Ser Lys Asn Leu Ala Pro Ile Ala Leu Asn Ala Gln Asp Asp Phe
        435                 440                 445

Ser Ser Thr Pro Ile Thr Met Asn Tyr Asn Gln Phe Leu Glu Leu Glu
    450                 455                 460

Lys Thr Lys Gln Leu Arg Leu Asp Thr Asp Gln Val Tyr Gly Asn Ile
465                 470                 475                 480

Ala Thr Tyr Asn Phe Glu Asn Gly Arg Val Arg Val Asp Thr Gly Ser
                485                 490                 495

Asn Trp Ser Glu Val Leu Pro Gln Ile Gln Glu Thr Thr Ala Arg Ile
            500                 505                 510

Ile Phe Asn Gly Lys Asp Leu Asn Leu Val Glu Arg Arg Ile Ala Ala
        515                 520                 525
```

-continued

```
Val Asn Pro Ser Asp Pro Leu Glu Thr Thr Lys Pro Asp Met Thr Leu
530                 535                 540

Lys Glu Ala Leu Lys Ile Ala Phe Gly Phe Asn Glu Pro Asn Gly Asn
545                 550                 555                 560

Leu Gln Tyr Gln Gly Lys Asp Ile Thr Glu Phe Asp Phe Asn Phe Asp
                565                 570                 575

Gln Gln Thr Ser Gln Asn Ile Lys Asn Gln Leu Ala Glu Leu Asn Val
            580                 585                 590

Thr Asn Ile Tyr Thr Val Leu Asp Lys Ile Lys Leu Asn Ala Lys Met
        595                 600                 605

Asn Ile Leu Ile Arg Asp Lys Arg Phe His Tyr Asp Arg Asn Asn Ile
    610                 615                 620

Ala Val Gly Ala Asp Glu Ser Val Lys Glu Ala His Arg Glu Val
625                 630                 635                 640

Ile Asn Ser Ser Thr Glu Gly Leu Leu Leu Asn Ile Asp Lys Asp Ile
                645                 650                 655

Arg Lys Ile Leu Ser Gly Tyr Ile Val Glu Ile Glu Asp Thr Glu Gly
                660                 665                 670

Leu Lys Glu Val Ile Asn Asp Arg Tyr Asp Met Leu Asn Ile Ser Ser
            675                 680                 685

Leu Arg Gln Asp Gly Lys Thr Phe Ile Asp Phe Lys Lys Tyr Asn Asp
        690                 695                 700

Lys Leu Pro Leu Tyr Ile Ser Asn Pro Asn Tyr Lys Val Asn Val Tyr
705                 710                 715                 720

Ala Val Thr Lys Glu Asn Thr Ile Ile Asn Pro Ser Glu Asn Gly Asp
                725                 730                 735

Thr Ser Thr Asn Gly Ile Lys Lys Ile Leu Ile Phe Ser Lys Lys Gly
                740                 745                 750

Tyr Glu Ile Gly Gly Pro Gly Pro Lys Asn Leu Asp Cys Trp Val Asp
            755                 760                 765

Asn Glu Glu Asp Ile Asp Val Ile Leu Lys Lys Ser Thr Ile Leu Asn
        770                 775                 780

Leu Asp Ile Asn Asn Asp Ile Ile Ser Asp Ile Ser Gly Phe Asn Ser
785                 790                 795                 800

Ser Val Ile Thr Tyr Pro Asp Ala Gln Leu Val Pro Gly Ile Asn Gly
                805                 810                 815

Lys Ala Ile His Leu Val Asn Asn Glu Ser Ser Glu Val Ile Val His
                820                 825                 830

Lys Ala Met Asp Ile Glu Tyr Asn Asp Met Phe Asn Asn Phe Thr Val
            835                 840                 845

Ser Phe Trp Leu Arg Val Pro Lys Val Ser Ala Ser His Leu Glu Gln
        850                 855                 860

Tyr Gly Thr Asn Glu Tyr Ser Ile Ile Ser Ser Met Lys Lys His Ser
865                 870                 875                 880

Leu Ser Ile Gly Ser Gly Trp Ser Val Ser Leu Lys Gly Asn Asn Leu
                885                 890                 895

Ile Trp Thr Leu Lys Asp Ser Ala Gly Glu Val Arg Gln Ile Thr Phe
            900                 905                 910

Arg Asp Leu Pro Asp Lys Phe Asn Ala Tyr Leu Ala Asn Lys Trp Val
        915                 920                 925

Phe Ile Thr Ile Thr Asn Asp Arg Leu Ser Ser Ala Asn Leu Tyr Ile
930                 935                 940
```

```
Asn Gly Val Leu Met Gly Ser Ala Glu Ile Thr Gly Leu Gly Ala Ile
            945                 950                 955                 960

Arg Glu Asp Asn Asn Ile Thr Leu Lys Leu Asp Arg Cys Asn Asn
                965                 970                 975

Asn Gln Tyr Val Ser Ile Asp Lys Phe Arg Ile Phe Cys Lys Ala Leu
            980                 985                 990

Asn Pro Lys Glu Ile Glu Lys Leu Tyr Thr Ser Tyr Leu Ser Ile Thr
        995                 1000                1005

Phe Leu Arg Asp Phe Trp Gly Asn Pro Leu Arg Tyr Asp Thr Glu
    1010                1015                1020

Tyr Tyr Leu Ile Pro Val Ala Ser Ser Ser Lys Asp Val Gln Leu
    1025                1030                1035

Lys Asn Ile Thr Asp Tyr Met Tyr Leu Thr Asn Ala Pro Ser Tyr
    1040                1045                1050

Thr Asn Gly Lys Leu Asn Ile Tyr Tyr Arg Arg Leu Tyr Asn Gly
    1055                1060                1065

Leu Lys Phe Ile Ile Lys Arg Tyr Thr Pro Asn Asn Glu Ile Asp
    1070                1075                1080

Ser Phe Val Lys Ser Gly Asp Phe Ile Lys Leu Tyr Val Ser Tyr
    1085                1090                1095

Asn Asn Asn Glu His Ile Val Gly Tyr Pro Lys Asp Gly Asn Ala
    1100                1105                1110

Phe Asn Asn Leu Asp Arg Ile Leu Arg Val Gly Tyr Asn Ala Pro
    1115                1120                1125

Gly Ile Pro Leu Tyr Lys Lys Met Glu Ala Val Lys Leu Arg Asp
    1130                1135                1140

Leu Lys Thr Tyr Ser Val Gln Leu Lys Leu Tyr Asp Asp Lys Asn
    1145                1150                1155

Ala Ser Leu Gly Leu Val Gly Thr His Asn Gly Gln Ile Gly Asn
    1160                1165                1170

Asp Pro Asn Arg Asp Ile Leu Ile Ala Ser Asn Trp Tyr Phe Asn
    1175                1180                1185

His Leu Lys Asp Lys Ile Leu Gly Cys Asp Trp Tyr Phe Val Pro
    1190                1195                1200

Thr Asp Glu Gly Trp Thr Asn Asp Lys Leu
    1205                1210

<210> SEQ ID NO 3
<211> LENGTH: 42
<212> TYPE: PRT
<213> ORGANISM: Artificial
<220> FEATURE:
<223> OTHER INFORMATION: B5R anchor

<400> SEQUENCE: 3

Ala Thr Tyr His Ile Ile Ile Val Ala Leu Thr Ile Met Gly Val Ile
1               5                   10                  15

Phe Leu Ile Ser Val Ile Val Leu Val Cys Ser Cys Asp Lys Asn Asn
            20                  25                  30

Asp Gln Tyr Lys Phe His Lys Leu Leu Pro
        35                  40

<210> SEQ ID NO 4
<211> LENGTH: 21
<212> TYPE: PRT
<213> ORGANISM: Artificial
```

```
<220> FEATURE:
<223> OTHER INFORMATION: Clostridium tetani TTC T cell epitope P30

<400> SEQUENCE: 4

Phe Asn Asn Phe Thr Val Ser Phe Trp Leu Arg Val Pro Lys Val Ser
1               5                   10                  15

Ala Ser His Leu Glu
            20

<210> SEQ ID NO 5
<211> LENGTH: 12
<212> TYPE: PRT
<213> ORGANISM: Artificial
<220> FEATURE:
<223> OTHER INFORMATION: Clostridium tetani TTC T cell epitope P4

<400> SEQUENCE: 5

Gly Gln Ile Gly Asn Asp Pro Asn Arg Asp Ile Leu
1               5                   10

<210> SEQ ID NO 6
<211> LENGTH: 9
<212> TYPE: PRT
<213> ORGANISM: Artificial
<220> FEATURE:
<223> OTHER INFORMATION: Clostridium tetani TTC T-cell epitope P21

<400> SEQUENCE: 6

Ile Arg Glu Asp Asn Asn Ile Thr Leu
1               5

<210> SEQ ID NO 7
<211> LENGTH: 15
<212> TYPE: PRT
<213> ORGANISM: Artificial
<220> FEATURE:
<223> OTHER INFORMATION: Clostridium tetani TTC T-cell epitope P23

<400> SEQUENCE: 7

Val Ser Ile Asp Lys Phe Arg Ile Phe Cys Lys Ala Asn Pro Lys
1               5                   10                  15

<210> SEQ ID NO 8
<211> LENGTH: 16
<212> TYPE: PRT
<213> ORGANISM: Artificial
<220> FEATURE:
<223> OTHER INFORMATION: Clostridium tetani TTC T-cell epitope P32

<400> SEQUENCE: 8

Leu Lys Phe Ile Ile Lys Arg Tyr Thr Pro Asn Asn Glu Ile Asp Ser
1               5                   10                  15

<210> SEQ ID NO 9
<211> LENGTH: 63
<212> TYPE: DNA
<213> ORGANISM: artificial
<220> FEATURE:
<223> OTHER INFORMATION: Ig kappa-chain leader sequence

<400> SEQUENCE: 9
atggagaccg acaccctgct gctgtgggtc ctgctcctgt gggtgcccgg cagcaccggc     60
gac                                                                  63
```

```
<210> SEQ ID NO 10
<211> LENGTH: 63
<212> TYPE: DNA
<213> ORGANISM: artificial
<220> FEATURE:
<223> OTHER INFORMATION: Ig kappa-chain leader sequence codon-optimized

<400> SEQUENCE: 10
atggaaacag atacactcct cctctgggtg ctcctgctct gggtcccagg atccacaggg      60
gat                                                                    63

<210> SEQ ID NO 11
<211> LENGTH: 63
<212> TYPE: DNA
<213> ORGANISM: artificial
<220> FEATURE:
<223> OTHER INFORMATION: Ig kappa-chainleader sequence codon optimized

<400> SEQUENCE: 11
atggaaaccg acactctcct gttatgggtt ttgcttcttt gggttcccgg aagtactggc      60
gat                                                                    63

<210> SEQ ID NO 12
<211> LENGTH: 63
<212> TYPE: DNA
<213> ORGANISM: artificial
<220> FEATURE:
<223> OTHER INFORMATION: Ig kappa-chain leader sequence codon optimized

<400> SEQUENCE: 12
atggaaactg atactctgct tctgtgggtg ctgctgctct gggtccctgg gagcacaggt      60
gac                                                                    63
```

RECOMBINANT POXVIRUS VECTOR COMPRISING TETANUS TOXIN FRAGMENT C

This application is a National Phase application under 35 U.S.C. §371 of International Application No. PCT/EP2012/004949, filed Nov. 30, 2012, and claims the benefit under 35 U.S.C. §119(e) of U.S. Provisional Patent Application 61/568,857 filed Dec. 9, 2011, the disclosure of which is incorporated by reference herein in its entirety.

FIELD OF INVENTION

The present invention relates to a recombinant poxvirus vector comprising tetanus toxin fragment C for improved immunogenicity of an antigen and related methods and uses. Specifically, the present invention generally relates to genetically engineered (recombinant) poxvirus vectors comprising a tetanus toxin fragment C (TTC) coding sequence operably linked to a bacterial antigenic determinant coding sequence as well as to methods and uses thereof, e.g., to affect an immune response in a subject.

BACKGROUND OF THE INVENTION

Tetanus toxin is a protein produced by *Clostridium tetani*, an anaerobic bacterium whose spores are commonly found in soil and animal waste. Tetanus toxin is an extremely potent neurotoxin which causes tetanus, a potentially fatal condition that affects the nervous system and is characterized by painful, uncontrolled muscle contractions. It is synthesized as a single polypeptide and is post-translationally modified to provide light and heavy chains linked by disulfide bonds.

The structure of tetanus toxin has been cloned and sequenced (Fairweather et al. (1986), J. Bacteriol. 165; 21-27). It is a 150 kD protein comprising 1315 amino acids. Papain digestion of the tetanus toxin results in the cleavage of the heavy chain to give two fragments, fragment B and C. Fragment C (also termed herein as tetanus toxin fragment C or "TTC") is a 50 kD polypeptide at the C-terminus which is capable of protecting mice against lethal challenge with tetanus toxin. Purified TTC is nontoxic in animals. Expression of Fragment C was carried out in *E. coli*, where it was fused to part of the *E. coli* trpE protein or to fragment B of tetanus toxin (Fairweather et al. (1987), Infection and Immunity 55: 2541-2545).

Other researchers have shown that TTC protective ability against tetanus can be successfully expressed in *Salmonella typhimurium* (Chatfield et al. (1992), Biotechnology, 10(8): 888-92). *Salmonella typhi*. vaccine strain CVD908, developed as a live oral typhoid vaccine has been used to deliver heterologous vaccine antigens. Specifically, the plasmid pTET containing the S1 subunit of pertussis toxin fused to fragment C was expressed at high levels in CVD908 when it is driven by the nirB promoter (Barry et al. (1996), Infection and Immunity 64(10): 4172-4181).

The adjuvant effect of TTC was first found when it was co-administered with the full length P28 glutathione S-transferase (GST) protein of *S. mansoni*. As disclosed in WO 94/03615 or WO 95/04151, expression of GST was increased when it is fused to TTC. It is taught that TTC acts as a carrier protein that "rescues" the expression of otherwise difficult to express proteins such as GST—a so-called "expression rescue" (see Gomez-Duarte et al. (1995), Vaccine 13:1596-1602 and Khan et al. (1994), Proc. Natl. Acad. Sci. USA 91:11261-11265). Because of the "expression rescue", it seems reasonable that the antigen titer against GST increases, since more GST or a form of the GST protein which is accessible for the immune system is produced. This assumption is corroborated by the finding that more copies of a TTC-GST fusion gene lead to an increased expression (see Example 5 of WO 94/03615). However, since TTC is a bacterial protein that was long ago applied as antigen to affect a protective immune response against *Clostridium tetani* (Boucher et al. (1994), Inf. Immunity 62(2):449-456), it is not surprising that the antibody titer is increased when another bacterial host cell (*Salmonella* sp.) of the same family (enterobacteriaceae) is used to express GST (Lee et al. (2000), Inf. Immunity 68(5)2503-2512). Lee et al. therefore conclude that TTC may be exploited as a potent tool to immunostimulate the production of antibodies directed against antigens in live vaccines, i.e., in living bacteria. In fact, the likelihood that the expression of a bacterial protein of one species in a bacterial host cell of another species is successful is unequally higher than expression of the bacterial protein in a non-bacterial host cell such as a virus.

As mentioned above, the phenomenon of "expression rescue" is only known for bacteria. In recombinant viruses, in particular poxviruses, applied as carriers for the expression of an antigen against which an immune response is desired, such a phenomenon is not known: Those of skill in the art use either multiple copies of the antigen or strong promoters that confer high expression of the antigen in order to "offer" an excess antigen to the immune system with the aim of affecting an immune response. Also, thus far, it was neither known nor believed to be possible to increase an immune response against an antigen, in particular against a bacterial antigen, by way of co-expressing the antigen together with a bacterial protein or even as a fusion protein with the bacterial protein when included in a recombinant virus. In fact, thus far, neither problems nor difficulties with the expression of an antigen in a virus acting as carrier for an antigen were discussed in the prior art, nor were difficulties known in obtaining a sufficient immune response against an antigen when a poxvirus was used as carrier to express the antigen.

Thus, while it was known in the art that a bacterial protein could "rescue" the expression of a an otherwise difficult to express antigenic protein in bacterial host cells, whereby an immune response against the antigenic protein could be enhanced, up to the present invention, any issue such as the expression of an otherwise difficult to express protein or the increment of the antibody titer against a desired antigen protein, was neither recognized nor known in the art when a poxvirus was used as carrier and which would thus have required improvement.

TTC is also known to contain T helper cell epitopes. These epitopes are exploited in that less immunogenic proteins are equipped with such epitopes with the aim of rendering them more immunogenic. Such an approach is, for example, described in WO 2008/045346: Specifically, the breast cancer antigen Her2/neu is modified by substituting amino acids to resemble a T cell epitope from TTC.

Another approach for rendering a cancer antigen more immunogenic is the fusion between TTC and DR4 or DR5. DR4 and DR5 are also known as TRAIL-R1 and TRAIL R2, both of which are capable of transducing an apoptotic signal to a cell expressing them. The idea described in WO 2010/054156 is to render DR4 and DR5 more immunogenic if fused to TTC.

Just another approach to render viral antigens more immunogenic is briefly envisaged in WO 92/22641: In particular, in passing by, this application suggests a coexpression approach of an HIV protein and TTC. However, apart from a mere hypothetical description, this application fails to provide any data on the suggested approach.

The present invention provides aspects and embodiments concerning recombinant poxvirus vectors comprising a TTC coding sequence, wherein said TTC coding sequence is operably linked to a coding sequence encoding a bacterial antigenic determinant. The present invention also provides methods and uses applying these recombinant poxvirus vectors in the treatment of subjects which would benefit from the administration of said recombinant poxvirus vectors. These aspects and embodiments are characterized and described herein, illustrated in the Examples, and reflected in the claims.

SUMMARY

For the first time, it is demonstrated that tetanus toxin fragment C can be expressed correctly with a target antigen in poxviruses to enhance antibody response to the antigen. It was surprisingly found that the antibody response to the antigen is improved in terms of magnitude and timing in the presence of toxin fragment C. Other advantages will become apparent to a skilled person in the art in view of the description, figures and claims.

Given the findings of the inventors, the present invention provides a system which confers a higher immune response against antigenic proteins. Said advantageous effect is preferably independent of the route of administration, i.e., not be limited to, e.g. oral or mucosal administration. Moreover, the technique provided by the present invention may even overcome problems with otherwise difficult to express proteins in poxvirus vectors.

Accordingly, in a first aspect, the present invention provides a recombinant poxvirus vector comprising an antigenic determinant coding sequence, in particular a bacterial one, and a tetanus toxin fragment C coding sequence. The tetanus toxin fragment C coding sequence and the antigenic determinant coding sequence are operably linked to each other.

In a further aspect, the present invention provides a composition comprising the recombinant poxvirus vector described herein. The composition is preferably a vaccine or pharmaceutical composition or is for use in a vaccine or in a pharmaceutical composition or as a medicament.

In another aspect, the present invention relates to the use of the recombinant poxvirus vector as pharmaceutical composition (or medicament) or vaccine.

In a yet further aspect, the present invention provides a (host) cell comprising the recombinant poxvirus vector described herein.

The recombinant poxvirus vector described herein can be used for increasing the antibody titer against an antigen and/or antigenic epitope, such as, for example, against a polypeptide from a bacterium, fungus, virus, prion, unicellular organism or parasite.

In yet another aspect, the invention provides a method of treating or preventing a pathological condition in a subject by administering the recombinant poxvirus vector or the vaccine produced according to the present invention.

The term "pathological condition" refers to a condition of a cell, tissue, organ, or multiple organs which departs or deviates from its normal conditions. It can be characterized by identifiable signs or symptoms. Pathological conditions may include, but are not limited to those resulting from persistent viral, bacterial, parasitic, fungal infections, prions and cancer. The pathological composition is preferably an infectious disease caused by a bacterium, fungus, virus, prion, unicellular organism or parasite in a subject. The subject is preferably a mammal, more preferably a human.

The present invention also relates to a method for affecting an immune response in a subject by providing and administering the recombinant poxvirus vector described herein to a subject. The subject is preferably a mammal, more preferably a human.

"Affecting an immune response" encompasses as preferred embodiment initiation and/or enhancement of an immune response.

In a still further aspect, the invention relates to a method of producing or generating the recombinant poxvirus as well as the antigens expressed from the recombinant poxvirus as subunit vaccine. Of course, the invention also relates to the recombinant poxviruses and antigens or one or more epitopes of the antigens produced from said methods.

Further, a kit comprising the recombinant poxvirus vector is also included in the present invention.

(A) The diagram shows geometric mean titers of neutralizing antibodies plus/minus standard error of the mean (GMT+/−SEM) after 3 vaccinations with the recombinant MVA as indicated. (B) The diagram shows geometric mean titers of antibodies plus/minus standard error of the mean (GMT+/−SEM).

Figure 2:
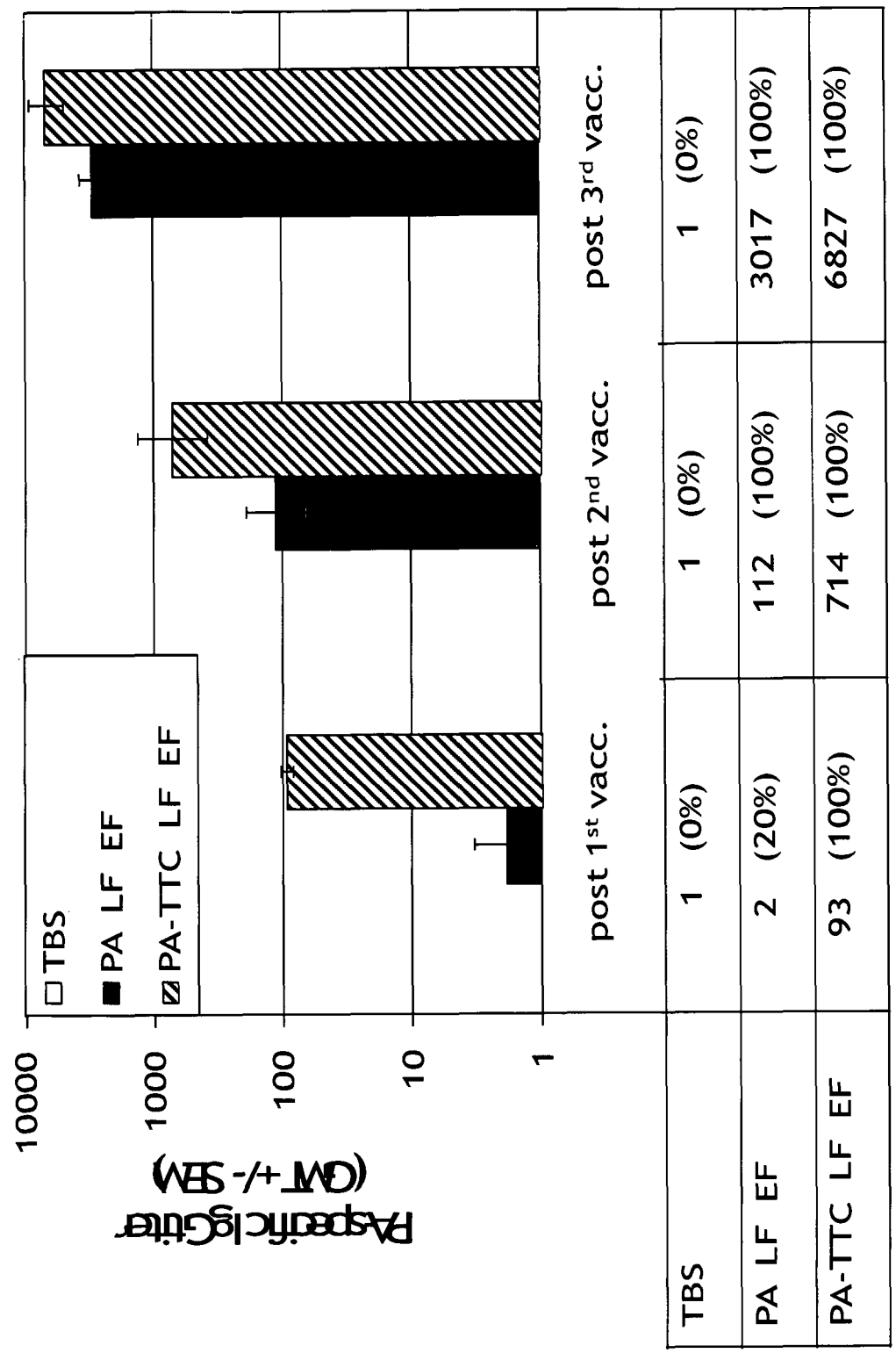

FIG. 2 demonstrates the results of an immunogenicity study of further MVA constructs in mice (MVA-mBN198, MVA-mBN212) after 1, 2 or 3 vaccinations. BALB/c mice were immunized three times in 4 week intervals with $1 \times 10^8$ $TCID_{50}$ of MVA-PA+LF+EF (MVA-mBN198) and MVA-PA-TTC+LF+EF (MVA-mBN212). Serum samples obtained from vaccinated mice were analyzed for protective antigen (PA)-specific antibodies by ELISA. The diagram shows geometric mean titers of antibodies (GMT) after 1, 2 or 3 vaccinations. In parentheses the percentage of seroconverted animals are indicated.

Figure 3:
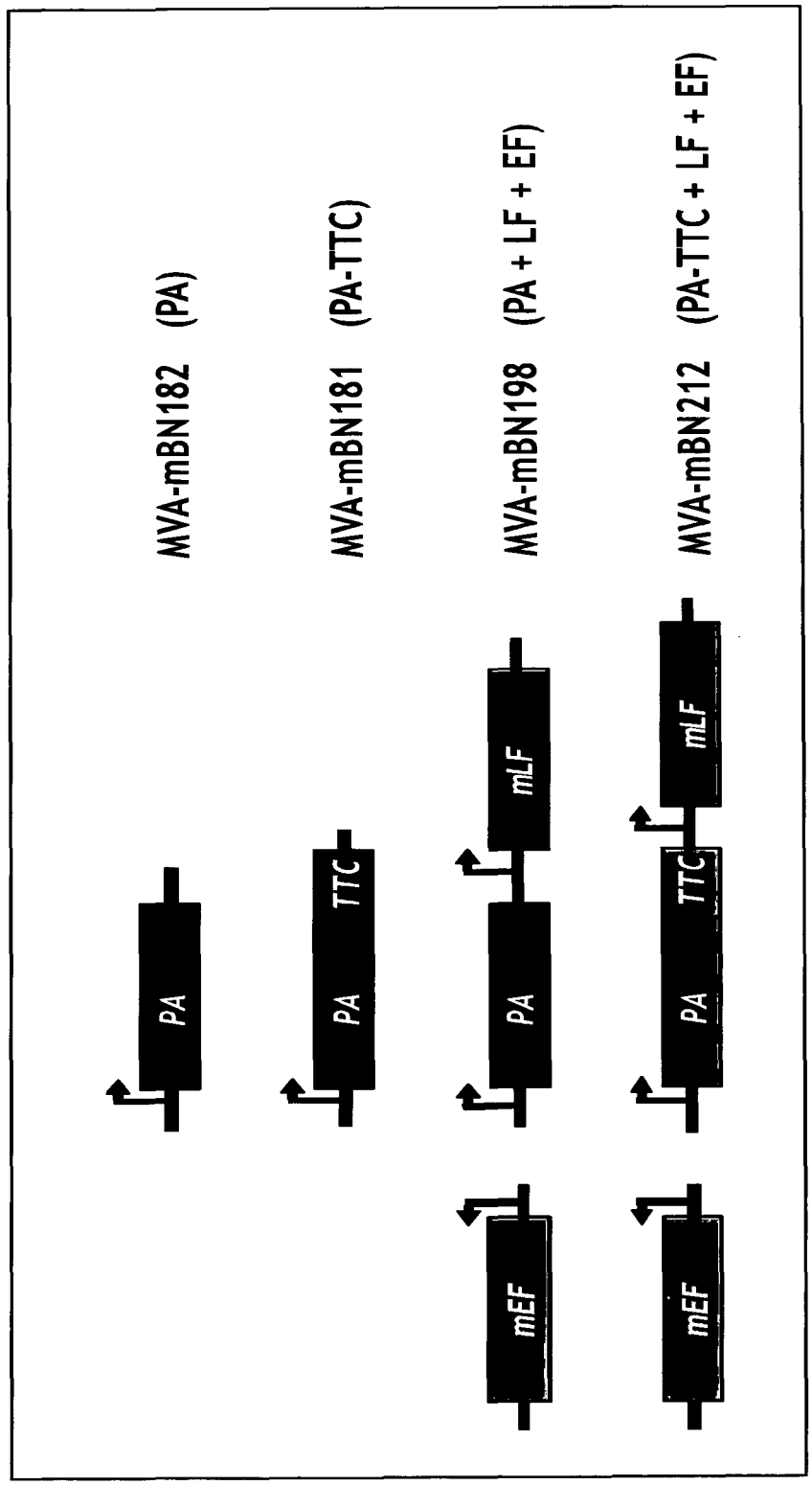

FIG. 3 depicts selected constructs in the present inventions. PA=protective antigen of *B. anthracis*; TTC=Tetanus toxin fragment C; (m)EF=(modified) edema factor of *B. anthracis*; (m)LF=(modified) lethal factor of *B. anthracis*. "Modified EF" and "modified LF" means that EF and LF, respectively, was changed, preferably to become inactivated.

Figure 4:
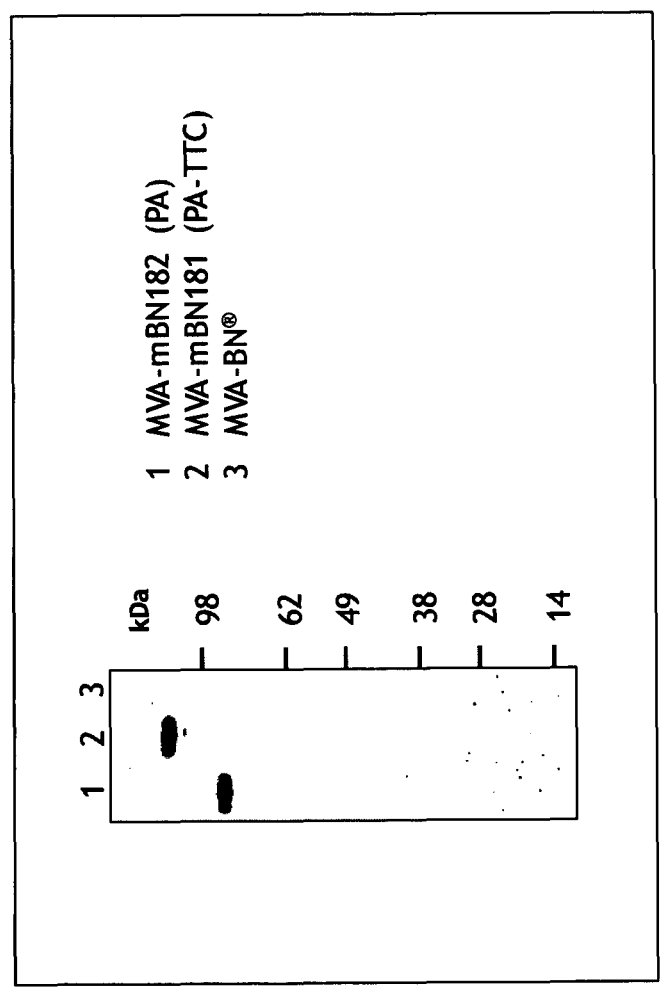

FIG. 4 shows the expression of MVA-PA (MVA-mBN182) and MVA-PA-TTC (MVA-mBN181) in HeLa cells. Lane 1=MVA-mBN182 (PA), Lane 2=MVA-mBN181 (PA-TTC), Lane 3=MVA-BN.

It must be noted that, as used herein, the singular forms "a", "an", and "the", include plural references unless the context clearly indicates otherwise. Thus, for example, reference to "an epitope" includes one or more of epitopes and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. When used herein the term "comprising" can be substituted with the term "containing" or "including" or sometimes when used herein with the term "having". Any of the aforementioned terms (comprising, containing, including, having), though less preferred, whenever used herein in the context of an aspect or embodiment of the present invention can be substituted with the term "consisting of".

When used herein "consisting of" excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Several documents are cited throughout the text of this specification. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

DETAILED DESCRIPTION OF THE INVENTION

There have been various attempts to provide a better expression system for expressing TTC fusion constructs. A fusion protein comprising TTC was found insoluble when expressed in *E coli*, although, when Fragment C is expressed alone, the resulting product is soluble (U.S. Pat. No. 5,443, 966). Extensive researches on TTC expression have been concentrated on bacterial expression systems, since TTC is derived from *Clostridium tetani*, an anaerobic bacterium of the genus *Clostridium*. It therefore seems reasonable to use bacterial expression systems for its expression. In particular, *salmonella* was found to be particularly suitable in conjunction with nirB promoter.

Although *salmonella*-based expression systems offers several advantages including easy manipulation, it is necessary to control the antigen expression level due to the rapid growth of *salmonella* in the host. Additionally, the risk of transmission of the *salmonella* bacteria may be an important concern.

The inventors have successfully demonstrated the expression of a functional TTC in poxvirus. TTC expressed presently was shown to enhance the immunogenicity of the antigen also expressed by the poxvirus. There is a general belief that the expression level must be sufficient to trigger the immune response of the host. However, the inventors have surprisingly found in this case, that TTC was able to enhance the immunogenicity of the antigen TTC-fusion protein expressed by the poxvirus vector although the expression level of the TTC-fusion protein was not significantly different from the expression of the protein without TTC. As an example, the PA protein from *B. anthracis* was used as model antigen. Yet, as said, PA is merely a model protein and, thus, the effect observed when TTC is expressed as fusion with PA can be plausibly generalized to each and every desired antigen fused with TTC, in particular to each and every other bacterial antigen. In particular, in bacteria it is shown that TTC massively enhanced the expression of otherwise difficult to express proteins (see Lee et al., discussed above). Thus, it is no surprise that a massively over-expressed TTC-fusion protein in bacteria also enhances antigen production against the fusion protein when live bacteria expressing the TTC-fusion protein are used as vaccine.

In contrast thereto, the inventors of the present invention unexpectedly found that expression of a TTC molecule operably linked to a bacterial antigenic determinant by a recombinant poxvirus significantly enhances the immune response against the antigenic determinant, though the protein is expressed at the same level as the protein alone without being linked to a TTC molecule. Notably and as a further surprising result a 100% seroconversion is already observed after a single immunization with the recombinant poxvirus expressing the TTC molecule operably linked to the bacterial antigenic determinant, while one immunization with a recombinant poxvirus expressing the antigenic determinant alone without being operably linked to a TTC molecule resulted in 0% seroconversion. A second immunization was necessary to result in 100% seroconversion in this case. The immune response found with the recombinant poxvirus according to the present invention can even be further boosted by a $2^{nd}$, $3^{rd}$ or further vaccination.

As demonstrated in more detail in FIG. 4, the expression of a TTC-PA fusion protein by a recombinant MVA is not at all higher than the expression of the PA protein alone. Accordingly, it is all the more surprising that, though the PA-TTC fusion protein is expressed at the same level as the PA protein alone, it can significantly and thus astonishingly enhance the immune response against the PA protein (see FIGS. 2 and 3). In fact, the skilled person knowing from bacteria that a massive increase in the expression of a TTC-fusion protein causes an enhanced immune response against the fusion protein could and would not have expected that a TTC-fusion protein expressed by a poxvirus, the expression of which is almost equal to the expression of the protein without TTC, could significantly express an immune response against the fusion protein.

Figure 1:
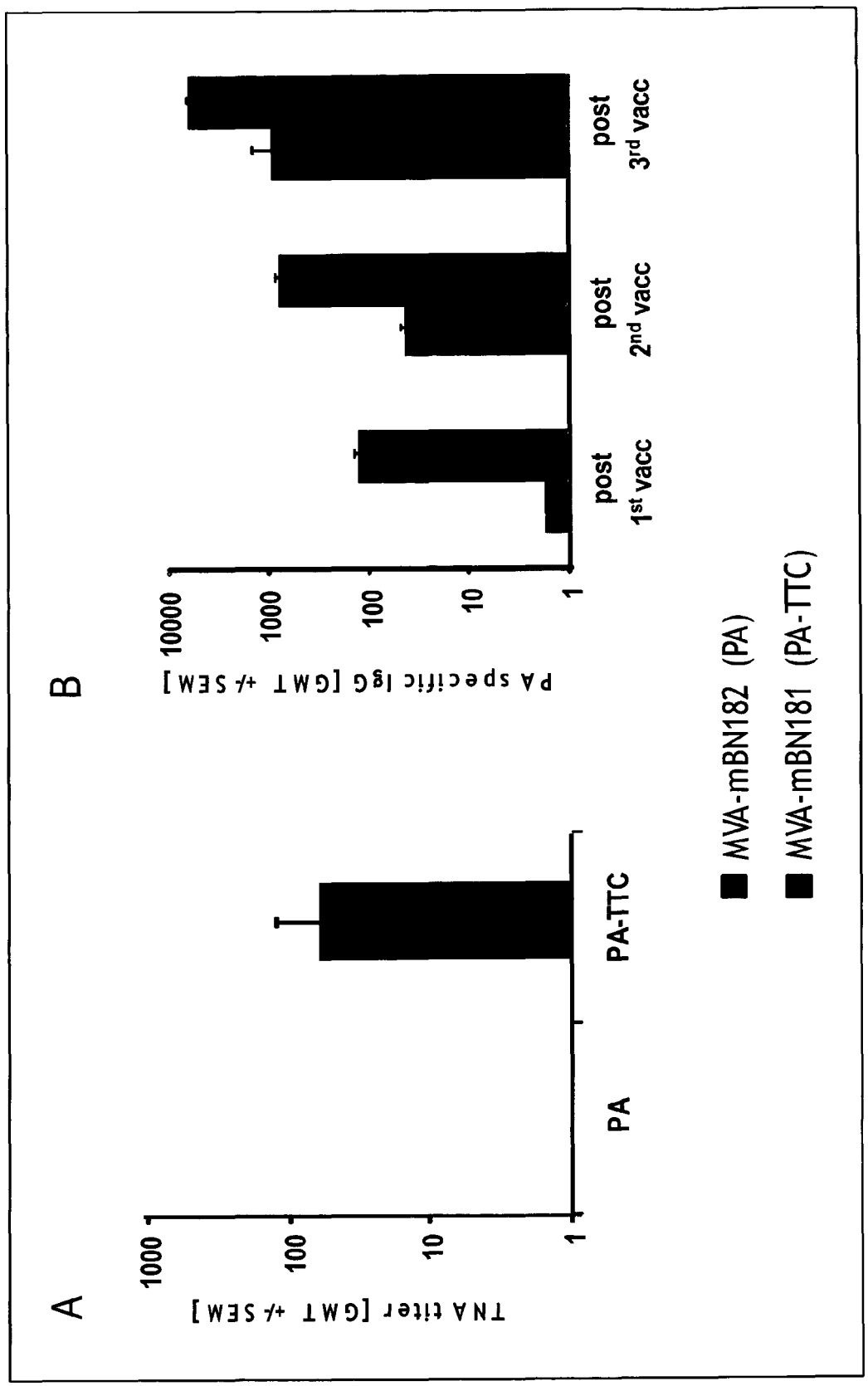
FIG. 1 illustrates the immunogenicity data of two recombinant poxvirus constructs in mice. BALB/c mice were immunized three times in 4 week intervals with $1 \times 10^8$ $TCID_{50}$ of MVA-PA (MVA-mBN182) and MVA-PA-TTC (MVA-mBN181). Serum samples obtained from mice vaccinated with recombinant modified vaccinia virus Ankara (MVA-mBN181 expressing PA-TTC and MVA-mBN182 expressing PA) were analyzed for protective antigen (PA)-specific antibodies by ELISA (FIG. 1B) and for neutralizing antibodies in a toxin neutralization assay (FIG. 1A).

The inventors have also discovered that the timing as well as the magnitude of antibody response to the expressed antigen can be improved (see FIGS. 1 and 2). Since poxvirus is propagated in eukaryotic cells, such cells will allow correct protein folding as well as the appropriate post-translational modifications, including glycosylation for certain antigens which requires such folding and/or modification as e.g. needed for viral, human and also other eukaryotic antigens. The present invention therefore provides several advantages compared to *salmonella*-based vaccines.

Antigen proteins from *B. anthracis* were used in the application to demonstrate the effect of TTC expression by poxviruses. As shown in FIG. 1, the addition of TTC in MVA-mBN181 (PA-TTC fusion) resulted in an earlier enhanced PA-specific antibody production compared to MVA-mBN182 (PA, for details of constructs, please see FIG. 3). Notably 100% seroconversion was already observed after a single immunization with MVA-mBN181 (PA-TTC), while one immunization with MVA-mBN182 (PA) resulted in 0% seroconversion and a second immunization was necessary to result in 100% seroconversion in this case. This response can be boosted by a $2^{nd}$ or $3^{rd}$ vaccination. In this example, PA antibody production can be measured by serological assays such as the anti-PA IgG enzyme-linked immunosorbent assay (ELISA), see Ngundi et al. (2010), Clin. Vaccine Immunol. 17(6):895-903. In the case of anthrax, Anti-PA IgG is used in the art to indicate vaccine efficacy, as anti-PA bodies confer protection to host cells by blocking the binding of anthrax toxin, as well as inhibit spore germination and increase the uptake and elimination of spores by macrophages (Welkos et al. (2001), Microbiol. 147:1677-1685). The anthrax toxin neutralizing assay (TNA) which quantifies the neutralization activity of anthrax lethal toxin is also often used.

FIG. 2 demonstrates a TTC-caused increase of antibody titer in response to antigens delivered by MVA (compare MVA-mBN212 to MVA-mBN198; for details of constructs, please see FIG. 3). An experiment comparable to the one shown in FIG. 1 was performed with another set of viruses as shown in FIG. 2. The effect of TTC can be observed although additional antigens of *B. anthracis* have been included in this vaccine strategy (EF and LF). Again the effect of TTC can be demonstrated by a high antibody response to PA and a very early onset of high antibody response after the first vaccination. Again seroconversion occurs at 100% after the first immunization with PA-TTC and additional antigens of *B. anthracis* (MVA-mBN212, see also FIG. 3), while in the control group with MVA-mBN198 without TTC, only one animal (20%) seroconverted after the first vaccination (FIG. 2). The immune response can be boosted by a $2^{nd}$ or $3^{rd}$ vaccination.

FIG. 1 compares the immunogenicity result of two different constructs, MVA-PA (MVA-mBN182) and MVA-PA-TTC (MVA-mBN181). As observed, TTC improved magnitude and kinetics of the antibody response against PA. This result is indeed surprising, since normally a skilled artisan would have used a stronger promoter or would have multiplied the copies of the desired antigen, just to name some of the usually applied measures. However, it could not have been expected that a bacterial protein enhances the immunogenicity of an antigen expressed in a recombinant poxvirus background.

In summary, the inventors have successfully demonstrated that poxviruses can be utilized to express TTC as immunostimulant to improve the antibody responses (both in terms of magnitude and timing) to antigens, in particular bacterial antigens, incorporated in the poxvirus. Serving as an example, the administration of MVA-based vaccines containing TTC is particularly useful in enhancing protection against anthrax infection in animal models.

None of the prior art approaches as described above provides any incentive or a starting basis or even envisages for exploiting TTC in combination with bacterial antigens, especially when bacterial antigens are expressed in a poxvirus. The prior art documents mentioned above do not suggest anything like this, since they are dealing either with cancer antigens or viral antigens. However, with bacterial antigens no need existed to improve immune responses thereto. In fact, the best example is the publication by Merkel et al. in PNAS Vol. 170, 2010, pp. 18091-18096: This publication reports on the development of a vaccinia-based dual vaccine against smallpox and anthrax. It exploits the PA-protein from anthrax in a vaccinia virus vector. As mentioned before, given the fact that the vaccine developed by Merkel et al. is said to be efficacious, no need existed in the prior art to perhaps improve a vaccinia virus based vaccine for the vaccination with a bacterial antigen. Thus, also in view of disclosure of the Merkel et al. document it was not foreseeable and must, therefore, be considered as being surprising that a faster and long-lasting immunogenicity of antigens, specifically bacterial antigens, could be achieved by just one or two immunizations, when co-expressed with TTC in a recombinant poxvirus.

Hence, the present invention provides a novel delivery system in which tetanus toxin fragment C may act as immunostimulant for DNA immunization or immunization with live vaccines. An immunostimulant elicits, enhances or potentiates an immune response (antibody and/or cell-mediated) to an antigen.

Thus, in a first aspect, the present invention provides a recombinant poxvirus vector comprising an antigenic determinant coding sequence operably linked to a tetanus toxin fragment C coding sequence. Recombinant poxvirus vectors according to the present invention can be used to express the antigen or antigenic determinant and the tetanus toxin fragment C molecule.

The recombinant poxvirus vector of the present invention is preferably attenuated. An "attenuated" poxvirus including also highly attenuated poxviruses as described herein, refers to a live poxvirus that has been modified so that its pathogenicity, virulence or contagiousness in the intended subject is reduced. A detailed review of attenuated poxvirus can also be found in U.S. Pat. No. 5,863,542.

The delivery of multiple antigens has been attempted by others with the use of fusion protein or different vectors. An advantage of using different vectors is the possibility of providing a host cell with different nucleic acid constructs in varying ratios. However, this requires the complicated process of co-transformation or co-transfection. It is therefore desirable to express multiple antigens for the same or different pathological conditions. Insertion sites in the poxvirus genome which are suitable for inserting heterologous genes are described in US 2011/0053260.

Accordingly, it is also envisaged by the present invention that, in addition to a TTC coding sequence operably linked to an antigenic determinant coding sequence, specifically to a bacterial one, the recombinant poxvirus vector comprises a further (e.g., second, third, fourth, etc.) antigenic determinant coding sequence that is operably linked to the TTC coding sequence. Accordingly, all embodiments pertaining to a TTC molecule, antigen or epitope of TTC and to an antigen/antigenic determinant/epitope linked to TTC also pertain to said further antigenic determinant coding sequence.

The recombinant poxvirus vector of the present invention may comprise any one of the following:
1) nucleic acids encoding (i) an antigen operably linked to (ii) tetanus toxin fragment C,
2) nucleic acids encoding (i) an antigen and an epitope thereof operably linked to (ii) tetanus toxin fragment C, 3) nucleic acids encoding (i) an epitope of an antigen operably linked to (ii) tetanus toxin fragment C,
4) nucleic acids encoding (i) an antigen operably linked to (ii) tetanus toxin fragment C and an epitope thereof,
5) nucleic acids encoding (i) an antigen operably linked to (ii) an epitope of the tetanus toxin fragment C,
6) nucleic acids encoding (i) an antigen and an epitope thereof operably linked to (ii) the tetanus toxin fragment C and an epitope thereof,
7) nucleic acids encoding (i) an antigen and an epitope thereof operably linked to (ii) an epitope of the tetanus toxin fragment C,
8) nucleic acids encoding (i) an epitope of an antigen operably linked to (ii) an epitope of the tetanus toxin fragment C,
9) nucleic acids encoding (i) an epitope of an antigen operably linked to (ii) the tetanus toxin fragment C and an epitope thereof,
10) nucleic acids encoding 1) to 9), but in the reverse order, i.e., element (ii) followed by element (i).

For easy understanding of the description, the above items 1-10 are sometimes referred to collectively as a nucleic acid encoding an antigen operably linked to a tetanus toxin fragment C.

The term "poxvirus" as used in the present application refers to poxviruses of the subfamily Chordopoxyirinae (vertebrate poxviruses) (Fields Virology/eds.: Fields, B. N., Knipe, D. M., Howley, P. M.; 3rd ed, see in particular chapter 83). The terms "Examples of poxviruses" include those belonging to the genera *Orthopoxvirus, Parapoxvirus, Avipoxvirus, Capripoxvirus, Lepripoxvirus, Suipoxvirus, Molluscipoxvirus* and *Yatapoxvirus*. Most preferred are poxviruses belonging to the genera *Orthopoxvirus* and *Avipoxvirus*.

A "virus vector" or "viral vector" refers to a viral particle having infectivity, which is also a carrier for introducing a gene into a cell. A "poxvirus vector" for purposes of the present invention may be recombinant naked viral DNA or the naked viral DNA encapsulated by viral envelope proteins. The poxvirus vector may be a part of or all of the viral genome.

In case of the naked viral DNA, a so-called DNA immunization is envisaged. The term "DNA immunization" refers to the introduction of a nucleic acid molecule encoding one or more selected antigens into a host cell for the in vivo expression of the antigen by a recombinant vector. In accordance with the present invention, DNA immunization employs poxviruses as vehicles that carry one or more nucleic acid molecules encoding antigenic determinants and antigens and/or epitopes thereof, respectively, and tetanus toxin fragment C molecule which may be a full-length molecule and/or a TTC epitope and/or any TTC molecule giving rise to the surprising result of immune response enhancement as described above.

Generally, a "recombinant" poxvirus as described herein refers to poxviruses that are produced by standard genetic engineering methods, i.e., poxviruses of the present invention are thus genetically engineered or genetically modified poxviruses. The term "recombinant poxvirus" or "recombinant MVA" thus includes poxviruses or modified vaccinia viruses which have stably integrated recombinant nucleic acid, preferably in the form of a transcriptional unit, in their genome. A transcriptional unit may include a promoter, enhancer, terminator and/or silencer. Recombinant poxviruses of the present invention may express heterologous polypeptides or proteins (antigens) upon induction of the regulatory elements.

In a preferred embodiment, the poxvirus vector is derived from vaccinia virus, and more preferably, from modified vaccinia virus Ankara (MVA). In particular, MVA-BN virus has preferably the capability of reproductive replication in vitro in chicken embryo fibroblasts (CEF) cells, but no capability of reproductive replication in the human keratinocyte cell line HaCat, the human bone osteosarcoma cell line 143B, the human embryo kidney cell line 293, and the human cervix adenocarcinoma cell line HeLa.

Preferably, the poxvirus vector is derived from poxviruses belonging to the Chordopoxyirinae subfamily. Attenuated poxviruses are particularly preferred because they do not replicate in the host but are able to introduce and express a targeted gene in infected cells. Poxviruses are especially suitable for DNA immunization because they have large capacity for insertion of sequences into the genome. Unlike other viruses, poxviruses replicate in the cytoplasm of the infected cell instead of the nucleus. Hence, the risk of insertional mutagenesis by integrating genetic material into the genome is minimized.

In other embodiments, the poxvirus is derived from avipoxviruses. Examples of avipoxviruses suitable for use in the present invention include any avipoxvirus such as fowlpoxvirus, canarypoxvirus, uncopoxvirus, mynahpoxvirus, pigeonpoxvirus, psittacinepoxvirus, quailpoxvirus, peacockpoxvirus, penguinpoxvirus, sparrowpoxvirus, starlingpoxvirus and turkeypoxvirus. Preferred avipoxviruses are canarypoxvirus and fowlpoxvirus.

Avipoxviruses are naturally host-restricted and productively replicate only in avian species and cells (Taylor et al (1995), Vaccine 13: 539-549,). Since avipoxviruses do not fully replicate in the human cells, there is no risk that the human being is harmed by productive virus replication. Various recombinant avipoxviruses have been constructed to express lentiviral gene products (U.S. Pat. No. 5,766,598), cytokines and/or tumor-associated antigens (U.S. Pat. No. 5,833,975) or rabies G glycoprotein (Taylor et al *Vaccine* 13:539-549, 1995). A recombinant canarypox virus expressing the four HIV genes gag, pol, env and nef has already been tested in clinical trials (Peters (2001), Vaccine 20: 688-705).

In addition, fowlpox recombinants were used to express the influenza virus HA and nucleocapsid proteins, the Marek's disease virus (MDV) gB glycoprotein and the Newcastle disease virus (NDV) fusion or HA glycoproteins to protect chickens against influenza, MDV and NDV, respectively (Webster et al. (1991), Vaccine 9: 303-7; Nazarian et al. (1992), J. Virol. 66: 1409-13; Taylor et al. (1990), J. Virol. 64: 1441-50; Edbauer et al. (1990), Virol. 179: 901-904).

The above use of poxviruses may, in accordance with the teaching of the present invention, be improved by introducing TTC sequence in the vector to enhance the potency of the vaccine.

Uses of the fowlpox vectors are not limited to avian animals. For example, a fowlpox recombinant expressing the rabies glycoprotein can protect mice, cats and dogs against rabies. Avipoxviruses do not replicate in non-avian species and can therefore be regarded as naturally attenuated for them.

An example for a canarypox virus is strain Rentschler. A plaque purified Canarypox strain termed ALVAC, the fowlpox-rabies glycoprotein recombinant (U.S. Pat. No. 5,766, 598), was deposited under the terms of the Budapest treaty with the American Type Culture Collection (ATCC), accession number VR-2547. Another Canarypox strain is the commercial canarypox vaccine strain designated LF2 CEP 524 24 10 75, available from Institute Merieux, Inc. A further example is deposited under the terms of the Budapest treaty with the American Type Culture Collection (ATCC), accession number VR-111.

A plaque-cloned isolate of an attenuated canarypox vaccine strain has been designated ALVAC (Tartaglia et al. (1992), Virol. 188: 217-232). ALVAC has a highly attenuated phenotype, and similar to NYVAC, exhibits negligible pathogenicity in newborn and immunocompromised mice. Although canarypox virus does not replicate in mammalian species, an ALVAC recombinant can be as potent in mammalian target species as a comparable replication-competent vaccinia virus recombinant. For example, dogs immunized with an ALVAC recombinant expressing the measles virus HA glycoprotein generated equivalent neutralizing antibody titres and were as resistant to CDV challenge as dogs immunized with a replication-competent vaccinia virus-measles HA recombinant (Taylor et al. (1992), Virol. 187: 321-328). ALVAC recombinants have additionally protected other mammalian target species against infectious agents. For example, ALVAC-RG protected dogs and cats against rabies (Taylor et al. (1991), Vaccine 9: 190-193). An ALVAC recombinant expressing the equine influenza virus (EIV) type A1 and type A2 HA glycoproteins protected horses against EIV (Taylor et al. (1992), The role of poxvirus vectors in influenza vaccine development. In: Proceedings of the Third International Symposium on Avian Influenza. University of Wisconsin-Madison Extension Duplicating Services). Furthermore, an ALVAC recombinant expressing the feline leukaemia virus (FeLV) gag and env proteins protected cats against FeLV (Tartaglia et al. (1993), J. Virol. 67: 2370-2375).

Examples of fowlpox viruses include strains FP-1, FP-5 and TROVAC (U.S. Pat. No. 5,766,598). In particular, FP-1 is a Duvette strain modified to be used as a vaccine in one day old chickens. The strain is a commercial fowlpox virus vaccine strain designated 0 DCEP 25/CEP67/2309 October, 1980 and is available from Institute Merieux, Inc. FP-5 is a commercial fowlpox virus vaccine strain of chicken embryo origin available from American Scientific Laboratories (Division of Schering Corp.) Madison, Wis., United States Veterinary License No. 165, serial No. 30321.

The above uses of avipox and fowlpox virus vector may therefore take advantage of the present invention by incorporating TTC in the virus genome.

Another preferred example of vaccinia virus is the highly attenuated vaccinia virus strain NYVAC derived from a plaque-cloned isolate of the Copenhagen vaccine strain (Tartaglia et al. (1992), Virol. 188: 217-232,). NYVAC does not produce detectable ulceration or induration at the site of inoculation and has negligible pathogenicity in newborn and immune-compromised mice. Furthermore, NYVAC is characterized by a dramatically reduced ability to replicate on a variety of human tissue culture cells, but retains the ability to induce strong immune responses to extrinsic antigens.

NYVAC recombinants have also protected target species against infectious challenges. A NYVAC recombinant expressing the preM and envelope proteins of Japanese encephalitis virus (JEV) protected pigs against JEV (Konishi et al. (1992), Virol. 190: 454-458,), a recombinant expressing the type A1 and type A2 haemagglutinin (HA) glycoproteins of equine influenza virus (EIV) protected horses against EIV (Tartaglia et al. (1994), in: Brown ed. Recombinant vectors in vaccine development. Dev. Biol. Stand, Basel: Karger; 82: 125-129,) and recombinants expressing the gB or gD glycoproteins of pseudorabies virus (PRV) protected pigs against PRV (Brockmeier et al. (1993), Vet. Micro. 38: 41-58,). NYVAC retains the immunogenicity and potency of a replication-competent vaccinia virus vector, and therefore represents a safe alternative to other poxviruses.

In particularly preferred embodiments, the vectors are derived from vaccinia viruses. Vaccinia virus strains have been used as vaccines in a global program against smallpox. It has double-stranded DNA genome of approximately 187,000 base pairs. Vaccinia virus is highly immune-stimulating and provokes strong B- (humoral) and T-cell mediated (cellular) immunity to both its own gene products and to many foreign gene products inserted in the genome. It is, therefore, an ideal vector for vaccines against smallpox and other infectious diseases or cancer in the form of recombinant vaccines. Advantages of vaccinia virus include the capacity to stably integrate over 25,000 base pairs of foreign DNA into the viral genome without loss of infectivity, a cytoplasmic site of gene expression, and a wide vertebrate host range in comparison to other poxviruses including members of the Avipox genus.

Vaccinia virus recombinants were shown to protect target species against vesicular stomatitis, canine distemper, rinderpest (also called cattle plague), pseudorabies and Venezuelan equine encephalitis (Mackett et al. (1985), Science 227: 433-436; Taylor et al. (1992), Virol. 187: 321-328; Yilma et al. (1998), Science 242: 1058-61; Riviere et al. (1992), J. Virol. 66: 3424-3434; Bowen et al. (1992), Vaccine Res. 1: 111-121). Vaccinia virus recombinants can be effectively employed against a variety of infectious diseases such as those described herein.

Most preferably, the poxvirus used as backbone for generating the recombinant virus according to the present invention is a modified vaccinia virus Ankara (MVA). When used herein, the term "modified vaccinia virus Ankara (MVA)", also referred to herein as "MVA", refers to any type of MVA strains derived from the dermal Vaccinia strain Ankara. MVA, in particular and most preferred MVA-BN, has preferably the capability of reproductive replication in chicken embryo fibroblasts (CEF), but no capability of reproductive replication in the human keratinocyte cell line HaCat (Boukamp et al (1988), J Cell Biol 106: 761-771), the human bone osteosarcoma cell line 143B (ECACC No. 91112502), the human embryo kidney cell line 293 (ECACC No. 85120602), and the human cervix adenocarcinoma cell line HeLa (ATCC No. CCL-2). In a preferred embodiment, the MVA-BN virus has an amplification ratio of greater than 500 in CEF cells. Tests and assay for these properties of MVA-BN are described in WO 02/42480 (US 2003/0206926) and WO 03/048184 (US 2006/0159699), both incorporated herein by reference.

A particularly preferred example of MVA is MVA-BN® as deposited at the European Collection of Cell Cultures (ECACC) under number V00083008.

The term "not capable of reproductive replication" is, for example, described in WO 02/42480, which also teaches how to obtain MVA having the desired properties as mentioned above. The term applies to a virus that has a virus amplification ratio at 4 days after infection of less than 1 using the assays described in WO 02/42480 or in U.S. Pat. No. 6,761,893. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells.

The term "fails to reproductively replicate" refers to a virus that has a virus amplification ratio at 4 days after infection of less than 1. Assays described in WO 02/42480 or in U.S. Pat. No. 6,761,893 (incorporated by reference) are applicable for the determination of the virus amplification ratio.

Preferably, an MVA has a virus amplification ratio at least two fold less, more preferably at least three fold less than MVA-575 in Hela cells and HaCaT cell lines. An MVA-BN virus can, for example, be derived by the further passage of a modified vaccinia virus Ankara (MVA), such as MVA-572 or MVA-575. WO 02/42480 discloses how vaccinia viruses are obtained having the properties of MVA-BN®. The highly attenuated MVA-BN® virus can be derived, e.g., by the further passage of a modified vaccinia virus Ankara (MVA), such as MVA-572 or MVA-575 and, optionally, by additional plaque purification steps.

MVA has been generated by more than 570 serial passages on chicken embryo fibroblasts of the dermal vaccinia strain Ankara (Chorioallantois vaccinia virus Ankara virus, CVA; for review see Mayr et al. (1975), Infection 3, 6-14) that was maintained in the Vaccination Institute, Ankara, Turkey for many years and used as the basis for vaccination of humans. However, due to the often severe post-vaccinal complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells (Mayr et al. (1975), Infection 3: 6-14). It was shown in a variety of animal models that the resulting MVA was avirulent (Mayr, A. & Danner, K. (1978), Dev. Biol. Stand. 41: 225-234). As part of the early development of MVA as a pre-smallpox vaccine, there were clinical trials using MVA-517 in combination with Lister Elstree (Stickl (1974), Prev. Med. 3: 97-101; Stickl and Hochstein-Mintzel (1971), Munch Med. Wochenschr. 113: 1149-1153) in subjects at risk for adverse reactions from vaccinia. In 1976, MVA derived from MVA-571 seed stock (corresponding to the $571^{st}$ passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. (1978), Zentralbl. Bacteriol. (B) 167: 375-390). MVA-572 was deposited at the European Collection of Animal Cell Cultures as ECACC V94012707.

As a result of the passaging used to attenuate MVA, there are a number of different strains or isolates, depending on the passage number in CEF cells. For example, MVA-572 was used in Germany during the smallpox eradication program, and MVA-575 was extensively used as a veterinary vaccine. MVA-575 was deposited on Dec. 7, 2000, at the European Collection of Animal Cell Cultures (ECACC) with the deposition number V00120707. The attenuated CVA-virus MVA (Modified Vaccinia Virus Ankara) was obtained by serial propagation (more than 570 passages) of the CVA on primary chicken embryo fibroblasts.

Even though Mayr et al. demonstrated during the 1970s that MVA is highly attenuated and avirulent in humans and mammals, certain investigators have reported that MVA is not fully attenuated in mammalian and human cell lines since residual replication might occur in these cells (Blanchard et al. (1998), J Gen Virol 79:1159-1167; Carroll & Moss (1997), Virology 238:198-211; U.S. Pat. No. 5,185, 146; Ambrosini et al. (1999), J Neurosci Res 55: 569). It is assumed that the results reported in these publications have been obtained with various known strains of MVA, since the viruses used essentially differ in their properties, particularly in their growth behaviour in various cell lines. Such residual replication is undesirable for various reasons, including safety concerns in connection with use in humans.

Strains of MVA having enhanced safety profiles for the development of safer products, such as vaccines or pharmaceuticals, have been developed by Bavarian Nordic: MVA was further passaged by Bavarian Nordic and is designated MVA-BN®. MVA as well as MVA-BN® lacks approximately 15% (31 kb from six regions) of the genome compared with ancestral CVA virus. The deletions affect a number of virulence and host range genes, as well as the gene for Type A inclusion bodies. A sample of MVA-BN® corresponding to passage 583 was deposited on Aug. 30, 2000 at the European Collection of Cell Cultures (ECACC) under number V00083008.

MVA-BN® can attach to and enter human cells where virally-encoded genes are expressed very efficiently. MVA-BN® is strongly adapted to primary chicken embryo fibroblast (CEF) cells and does not replicate in human cells. In human cells, viral genes are expressed, and no infectious virus is produced. MVA-BN® is classified as Biosafety Level 1 organism according to the Centers for Disease Control and Prevention in the United States. Preparations of MVA-BN® and derivatives have been administered to many types of animals, and to more than 2000 human subjects, including immune-deficient individuals. All vaccinations have proven to be generally safe and well tolerated.

"Derivatives" or "variants" of MVA refer to viruses exhibiting essentially the same replication characteristics as MVA as described herein, but exhibiting differences in one or more parts of their genomes. A derivative or variant of MVA-BN fails to reproductively replicate in vivo in humans and mice, even in severely immune suppressed mice. More specifically, a derivative or variant of MVA-BN has preferably also the capability of reproductive replication in chicken embryo fibroblasts (CEF), but no capability of reproductive replication in the human keratinocyte cell line HaCat (Boukamp et al (1988), J Cell Biol 106: 761-771), the human bone osteosarcoma cell line 143B (ECACC No. 91112502), the human embryo kidney cell line 293 (ECACC No. 85120602), and the human cervix adenocarcinoma cell line HeLa (ATCC No. CCL-2). Additionally, a derivative or variant of MVA-BN has a virus amplification ratio at least two fold less, more preferably three-fold less than MVA-575 in Hela cells and HaCaT cell lines. Tests and assay for these properties of MVA variants are described in WO 02/42480 (US 2003/0206926) and WO 03/048184 (US 2006/0159699), both incorporated herein by reference.

In another aspect, the MVA virus may be a mutant MVA, such as the deleted chorioallantois vaccinia virus Ankara (dCVA). A dCVA comprises del I, del II, del III, del IV, del V, and del VI deletion sites of the MVA genome. The sites are particularly useful for the insertion of multiple heterologous sequences. The dCVA can reproductively replicate (with an amplification ratio of greater than 10) in a human cell line (such as human 293, 143B, and MRC-5 cell lines), which then enable the optimization by further mutation useful for a virus-based vaccination strategy (see WO 2011/092029).

The advantages of MVA-based vaccine include their safety profile as well as availability for large scale vaccine production. Preclinical tests have revealed that MVA-BN® demonstrates superior attenuation and efficacy compared to other MVA strains (WO02/42480). MVA viruses such as that deposited at ECACC under number V00083008 have the capability of reproductive replication in vitro in chicken embryo fibroblasts (CEF), but no capability of reproductive replication in the human keratinocyte cell line HaCat, the human embryo kidney cell line 293, the human bone osteosarcoma cell line 143B, and the human cervix adenocarcinoma cell line HeLa. MVA-BN® strains fail to replicate in a mouse model that is incapable of producing mature B and T cells, and as such is severely immune compromised and highly susceptible to a replicating virus. An additional property of MVA-BN® strains is the ability to induce substantially the same level of immunity in vaccinia virus prime/vaccinia virus boost regimes when compared to DNA-prime/vaccinia virus boost regimes.

The recombinant MVA-BN viruses, the most preferred embodiment herein, are considered to be safe because of their distinct replication deficiency in mammalian cells and their well-established avirulence. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

Other poxviruses such as racoonpox and mousepox may be employed in the present invention, for example, for the manufacture of wild-life vaccine. Members of the capripoxvirus and leporipox are also included herein as they may be useful as vectors for cattles and rabbits, respectively.

The term "isolated" refers to a nucleic acid or polypeptide removed from its naturally occurring environment. Nucleic acids, polypeptides and proteins as referred to herein are preferably "isolated nucleic acids", "isolated polypeptides" and "isolated proteins", respectively.

When used herein "operably linked" refers to the juxtaposition where two or more components are in a relationship permitting them to be translated and function in the intended manner. Two sequences can be "operably linked" by fusing them directly together or inserting a linker sequence in between. A linker sequence refers to a short sequence that may be transcribed into a short (e.g., about 1-20 amino acids) sequence of amino acids that is not part of either of the two polypeptide sequences being joined. In other words, a linker polypeptide sequence has its amino-terminal end joined to one polypeptide and its carboxyl-terminal end joined to another polypeptide.

Alternatively, two sequences can be translationally coupled. Translational coupling, also called conjugated translation, is known in the art. Translational coupling was described for the first time by Oppenheim et al. for the tryptophan operon in *E. coli* (Oppenheim et al. (1980), Genetics 95: 789-795). Generally, it refers to situations where translation of a gene in a polycistronic mRNA is dependent on the translation of a contiguous upstream gene. The translation of two genes can be mediated via the same ribosome. The ribosome terminates translation at a stop codon in the upstream sequence and scans the downstream sequence, beginning the new translation at a start codon in the vicinity of this stop codon. This scanning operation by the ribosome proceeds in both directions, such that continuation of synthesis may be initiated at a start codon which overlaps with the stop codon of the preceding coding sequence. The translation of a downstream coding sequence requires translational termination of an upstream sequence at (or near) the initiation codon. In other words, the ribosome must translate the upstream gene completely before it can begin to translate the gene or genes situated towards the downstream gene. The ribosome is unable to initiate translation of the downstream gene directly. To achieve this, by way of example, a construct may be used that starts with a start ATG followed by the first sequence encoding the antigenic determinant and antigen or antigenic epitope, respectively, followed by a further ribosome binding site and a sequence which represents an overlap between a stop and a start codon (TGATG for example), and finally, the second sequence encoding a TTC coding sequence. Thus, TTC is only translated when the antigen or antigenic epitope is translated before and separately therefrom. Translational coupling may be facilitated by way of introducing so-called internal ribosome entry sites (IRES) between element (i) and (ii), with element (i) being a nucleic acid encoding a protein comprising the full-length TTC antigen and/or an epitope thereof and/or any TTC molecule resulting in the surprising effect of immune response enhancement as described further above, and element (ii) being a nucleic acid encoding an antigen and/or an epitope thereof.

The term "antigenic determent" or "antigen" refers to a molecule which contains one or more epitopes that stimulate a host's immune system to make a cellular antigen-specific immune response, or a humoral antibody response. Antigens may include proteins, polypeptides, antigenic protein fragments and the like. Furthermore, the antigen can be derived from any known virus, bacterium, parasite, prion, plants, protozoans, or fungus and can be a whole organism. The term also includes tumor antigens and antigenic determinants, respectively. Synthetic antigens such as polyepitopes, flanking epitopes, and other recombinant or synthetically derived antigens are also included in this application. In a preferred embodiment, the antigen in the present invention is a polypeptide or protein.

In relation to the term "epitope", the term "antigen" refers to a (longer) sequence, in particular a (longer) amino acid sequence or protein sequence, whereas the phrase "antigenic epitope" or "an epitope of the antigen" encompasses a stretch of shorter sequence from the longer sequence. The term "antigen" thus encompasses epitopes. The term "antigen" also includes variants of proteins, polypeptides, and antigenic protein fragments as described herein. Also, the term "antigen" encompasses sequences identical to the native sequence as well as modification to the native sequence, such as deletions, additions, insertions and substitutions. Preferably, an antigen variant has at least about 50%, at least about 60% or 65%, at least about 70% or 75%, at least about 80%, 81%, 82%, 83%, 84%, 85%, 86%, 87%, 88%, or 89%, more typically, at least about 90%, 91%, 92%, 93%, or 94% and even more typically at least about 95%, 96%, 97%, 98% or 99%, most typically, at least about 99% amino acid identity with the reference antigen (i.e. the antigen from which it is derived).

An epitope, also termed herein as "antigenic epitope", forms part of the antigen that still elicit an immune response in a host. An epitope is, however, not limited to the exact sequence of the antigen from which it is derived. Thus, the term "epitope" encompasses sequences identical to the native sequence as well as modification to the native sequence, such as deletions, additions, insertions and substitutions. Preferably, an epitope variant have at least about 50%, at least about 60% or 65%, at least about 70% or 75%, at least about 80%, 81%, 82%, 83%, 84%, 85%, 86%, 87%, 88%, or 89%, more typically, at least about 90%, 91%, 92%, 93%, or 94% and even more typically at least about 95%, 96%, 97%, 98% or 99%, most typically, at least about 99% amino acid identity with the reference epitope (i.e. the epitope from which it is derived).

Techniques for determining sequence identity between two nucleic acids and amino acids are known in the art. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

"Percent (%) amino acid sequence identity" with respect to antigens or epitopes described herein is defined as the percentage of amino acid residues in a candidate sequence that are identical with the amino acid residues in the reference sequence (i.e. the antigen or epitope from which it is derived), after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

The same is applicable to "percent (%) nucleotide sequence identity", mutatis mutandis.

For example, an appropriate alignment for nucleic acid sequences is provided by the local homology algorithm of Smith and Waterman, (1981), Advances in Applied Mathematics 2: 482-489. This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986), Nucl. Acids Res. 14(6): 6745-6763. An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+ GenBank CDS translations+Swiss protein+Spupdate+PIR. Details of these programs can be found at the following internet address: http://http://blast.ncbi.nlm.nih.gov/.

Epitopes are also known as antigenic determinants. Epitopes can be mapped using protein microarrays, and with the ELISPOT or ELISA technique. Epitope mapping is, thus, the process of identification and characterization of the minimum molecular structures that are able to be recognized by the immune system elements, mainly T and B cells. A collection of in vivo and in vitro methodologies are used for epitope mapping and are well known to the skilled practitioner. Among the most used are binding assay, ELISPOT, HLA transgenic mice and prediction software. A skilled person is capable, based on the common knowledge in the field, to select suitable epitopes for their application in the present invention. An "epitope" when used herein encompasses a fragment of an antigen, said fragment is preferably capable of eliciting an immune response. Preferably, said epitope encompasses at least 3, 4, 5, 6, 7, 8, 9, 10, 15, 20, or amino acids of an antigen. Preferably, said 3, 4, 5, 6, 7, 8, 9, 10, 15, 20, or 25 amino acids of said antigen are contiguous amino acids of said antigen, however, said amino acids may also be non-contiguous.

A "variant" of an antigen or epitope is one that differs from the reference antigen or epitope, but is still capable of eliciting an immune response including an antibody response in a subject. This can be determined by known methods in the art and additionally by the methods described in the Examples. A variant and reference antigen or epitope may differ by one or more modifications such as amino acid deletion, insertions and/or substitutions. It is also preferred that a variant is inactive as regards its natural (i.e., wild-type) biological activity/function.

Variants of an antigen or epitope may occur naturally, such as allelic variants, or non-naturally, such as by substitutions, preferably conservative substitution, additions, or deletions. Techniques such as conservative substitutions or silent mutations such as silent substitutions, additions, and deletions can be used to obtain variants. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are preferably in the range of about 1 to 50 amino acids. The variation allowed may be experimentally determined by systematically making insertions, deletions, or substitutions of amino acids in a polypeptide molecule using recombinant DNA techniques and assaying the resulting recombinant variants for activity. It is preferred that not more than 50, 40, 30, 20 or 10 modifications are made in a variant as described herein.

Variants as described herein have, preferably, an amino acid sequence with at least about 50%, at least about 60% or 65%, at least about 70% or 75%, at least about 80%, 81%, 82%, 83%, 84%, 85%, 86%, 87%, 88%, or 89%, more typically at least about 90%, 91%, 92%, 93%, or 94% and even more typically at least about 95%, 96%, 97%, 98% or 99%, most typically at least about 99% amino acid identity with the reference polypeptide.

Variants of the reference antigens as described herein, may also be fragments or epitopes of the reference antigen, such as sequences which include one or more antigenic epitopes from the reference antigen.

The recombinant poxvirus vector in the present invention can be used in a method of increasing the antibody titer against an antigen and/or antigenic epitope, wherein said method comprises the step of administering the recombinant poxvirus vector to a subject. Any antigen can be employed in the recombinant poxvirus vector, uses or methods of the present invention to which one wishes to affect the immune response in the subject. Antigens and/or epitopes in the present invention can be a polypeptide and/or epitope thereof from a bacterium, fungus, virus, unicellular organism, prion or parasite and can, thus, be derived from any organism or microorganism, such as any virus, any bacterium, any fungus, any unicellular organism, any prion or parasite.

An antigen/antigenic determinant "derived" from a pathogen can be an active fragment or variant of the full-length antigen.

Preferably, the nucleic acid sequences encoding the antigen and antigenic determinant, respectively, are derived from an infectious or pathogenic microorganism, including different strains or clades, variants, subtypes or serotypes of the microorganism. The terms "strain" or "clade" are technical terms, well known to the practitioner, referring to the taxonomy of microorganisms. The taxonomic system classifies all so far characterized microorganisms into the hierarchic order of Families, Genera, Species, Strains (Fields Virology, ed. by Fields B. N., Lippincott-Raven Publishers, 4th edition 2001). The term "strain" or "clade" describes a microorganism, i.e. virus, which shares the common characteristics, like basic morphology or genome structure and organization, but varies in biological properties, like host range, tissue tropism, geographic distribution, attenuation or pathogenicity. The term "variants" or "serotypes" further distinguishes between members of the same strain, also called subtypes, which show individual infection spectra or antigenic properties due to minor genomic variations.

According to further embodiments of the present invention, the antigens are preferably derived from viruses. Representative examples of viruses include, but are not limited to, HIV (HIV-1 or HIV-2), herpes viruses (e.g. HSV1 or HSV2), cytomegalovirus (CMV), Epstein Barr virus (EBV), hepatitis viruses (e.g. hepatitis A virus (HAV), HBV, HCV and hepatitis E virus), flaviviruses (e.g. Yellow Fever Virus), varicella-zoster virus (VZV), paramyxoviruses, respiratory syncytial viruses (RSV), parainfluenza viruses, measles virus, influenza viruses, and papillomaviruses. Particularly preferred examples of virus antigens are derived from retroviruses (including HIV-1 and HTLV), herpesviruses (including cytomegalovirus), flaviviruses (including dengue virus), orthomyxoviruses, paramyxoviruses (including measles virus, mumps virus, respiratory syncytial virus), togaviruses (including rubella virus), hepatitis viruses, hepadnaviruses, influenza virus, picornaviruses (including poliovirus), coronaviruses, bunyaviruses, arenaviruses, filoviruses or from other viruses causing hemorrhagic fever.

In another embodiment, the antigen is the NS1 gene of Dengue virus. Antigens may of course be derived from different serotypes of the Dengue virus, such as from one of the Dengue virus serotypes.

In another preferred embodiment, the two, preferably three nucleotide sequences encoding Ebola virus (EBOV) proteins such as EBOV glycoproteins (GP). In a particular preferred embodiment, the nucleotide sequences encode glycoprotein precursor proteins from the EBOV strains EBOV-B (Bundibugyo), EBOV-S (Sudan ebolavirus strain Gulu) and EBOV-Z (Zaire ebola virus strain Mayinga).

In another embodiment, the antigens are selected from bacteria. Representative examples of suitable bacteria include, but are not limited to, *Neisseria* (e.g. *N. gonorrhea* and *N. meningitidis*); *Bordetella* (e.g. *B. pertussis, B. parapertussis* and *B. bronchiseptica*), *Mycobacteria* (e.g. *M. tuberculosis, M. bovis, M. leprae, M. avium, M. paratuberculosis, M. smegmatis*); *Legionella* (e.g. *L. pneumophila*); *Escherichia* (e.g. enterotoxic *E. coli*, enterohemorragic *E. coli*, enteropathogenic *E. coli*); *Shigella* (e.g. *S. sonnei, S. dysenteriae, S. flexnerii*); *Salmonella* (e.g. *S. typhi, S. paratyphi, S. choleraesuis, S. enteritidis*); *Listeria* (e.g. *L. monocytogenes*); *Helicobacter* (e.g. *H. pylori*); *Pseudomonas* (e.g. *P. aeruginosa*); *Staphylococcus* (e.g. *S. aureus, S. epidermidis*); *Enterococcus* (e.g. *E. faecalis, E. faecium*); *Bacillus* (e.g. *B. anthracis*); *Corynebacterium* (e.g. *C. diphtheriae*), and *Chlamydia* (e.g. *C. trachomatis, C. pneumoniae, C. psittaci*). Representative examples of parasites include without limitation *Plasmodium* (e.g. *P. falciparum*); *Toxoplasma* (e.g. *T. gondii*); *Leishmania* (e.g. *L. major*); *Pneumocystis* (e.g. *P. carinii*); and *Schistostoma* (e.g. *S. mansoni*). Representative examples of fungi include, but are not limited to, *Candida* (e.g. *C. albicans*) and *Aspergillus*.

Nucleic acid sequences encoding the antigen or an epitope thereof are preferably codon optimized. A "codon-optimized" nucleic acid sequence refers to a nucleic acid sequence containing codons that are replaced by codons preferred by the desired host cell, preferably a human host cell. A nucleic acid sequence is converted into a codon-optimized nucleic acid sequence having an identical translated polypeptide sequence, but with alternative codon usage, in particular using the most frequently codons of the targeted organism. The method of creating a codon-optimized nucleic acid sequence of an antigen generally includes identifying codons in the naturally occurring sequence of an antigen that are commonly not associated with high expressing genes in the target organism and replacing them with codons that are known to be widely used in gene expression of the target organism. A codon-optimized nucleic acid sequence may show improved expression over the naturally occurring sequence in the desired host cell. Whether a codon optimized sequence will induce an improvement in the protein production over the non-optimized sequence can be examined by a skilled person.

Codon optimization avoids the use of rare codons for a desired host, since rare codons may block or reduce expression of the encoded protein. Also, substitutions that may introduce nucleic acid signals for the desired host are preferably avoided. Such signals include, but are not limited to, splice signals, termination signals, and initiation signals. Preferably, the following sequence motifs are avoided depending on the type of vector utilized, e.g., the vaccinia virus early transcription termination signal needs not to be avoided in many other vectors, internal TATA-boxes, chi-sites, and ribosomal entry sites; AT-rich and GC-rich sequence stretches; ARE, INS, and CRS sequence elements; repeat sequences and RNA secondary structures; (cryptic) splice donor and acceptor sites, and branch points; and vaccinia early transcription termination signals: (TTTTTNT).

Techniques for codon optimization are known in the art. Substitution of nucleotides with different nucleotides refers to the technical or artificial replacement of nucleotides by other nucleotides. Preferably, substituted nucleotides do not alter the encoded amino acid sequence. Substitution can be performed by identifying codons in two or more homologous nucleotide sequences encoding the same amino acids and altering codons in one of the two or more homologous nucleotide sequences such that the codons still encodes the same amino acids. The alterations can be made in one, both or all of the homologous nucleotide sequences.

Exemplary antigens/antigenic determinants include *Mycobacterium leprae* antigens; *Rickettsia* antigens; *Coxiella* antigens; malaria sporozoite and merozoite proteins, such as the circumsporozoite protein from *Plasmodium berghei* sporozoites; diphtheria toxoids; tetanus toxoids; *Leishmania* antigens; *Salmonella* antigens; *E. coli* antigens; *Listeria* antigens; *Borrelia* antigens, including the OspA, OspB, OspC, dbpA, dbpB, Fla, VIsE and BBK32 antigens of *Borrelia burgdorferi; Franciscella* antigens; *Mycobacterium africanum* antigens; *Mycobacterium* intracellular antigens; *Mycobacterium avium* antigens; *Treponema* antigens; *Schistosome* antigens; *Filaria* antigens; *Pertussis* antigens; *Staphylococcus* antigens; and parainfluenza virus antigens; measles virus antigens; *Bordatella* antigens; *Hemophilus* antigens; *Streptococcus* antigens, including the M protein of *S. pyogenes* and pneumococcus antigens such as *Streptococcus pneumoniae* antigens; mumps virus antigens; hepatitis virus antigens; *Shigella* antigens; *Neisseria* antigens; rabies antigens; polio virus antigens; Rift Valley Fever virus antigens; dengue virus antigens; measles virus antigens; rotavirus antigens; Human Immunodeficiency Virus (HIV) antigens, including the gag, poi, and env proteins; respiratory syncytial virus (RSV) antigens; snake venom antigens; human tumor antigens; and *Vibrio cholera* antigens. Other suitable antigens include a *Borrelia* antigen, e.g., OspA, OspC, OspB, OspD; a pneumococcal antigen, e.g., PspA; an influenza (Flu) antigen such as HA; a pertussis or whooping cough antigen such as the pertussis 69 KD polypeptide; a hepatitis antigen, e.g., hepatitis B antigen such as hepatitis B surface antigen; a *Helicobacter pylori* antigen such as urease; a rabies virus antigen, e.g., rabies G antigen; a flavivirus antigen, e.g., a Japanese encephalitis virus, Dengue virus or yellow fever virus antigen; a chicken pox virus antigen; a diphtheria antigen; a *C. tetani* antigen, e.g., tetanus toxoid; a mumps virus antigen; a measles virus antigen; a malaria antigen; a herpes virus antigen, such as an alpha herpesvirus, beta herpesvirus or gamma herpesvirus antigen, e.g., a herpes virus glycoprotein, for instance an equine herpes virus antigen, e.g., gpl3, gpl4, gD, gp63, orgE, a pseudorabies virus antigen, e.g., gp50, gpll, gplll, gpl, a herpes simplex virus antigen, e.g., gC, gD, a bovine herpes virus antigen, e.g., gl, a feline herpes virus antigen, e.g., gB, an Epstein-Barr virus antigen, e.g., gp220, gp340, or gH, or a human cytomegalovirus antigen, e.g., gB; a human immunodeficiency virus antigen, e.g., gpl60 or gpl20; a simian immunodeficiency virus antigen; a bovine viral diarrhea virus antigen; an equine influenza virus antigen; a feline leukemia virus antigen; a canine distemper virus antigen, e.g., HA or F glycoproteins; a canine adenovirus antigen, e.g., canine adenovirus type 2 antigen; a canine coronavirus antigen; a canine parainfluenza antigen; a canine parvovirus antigen; a Hantaan virus antigen; an avian influenza virus antigen e.g., a nucleoprotein antigen; a Newcastle Disease virus antigen, e.g., F, HN; an antigen of rous associated virus, e.g., an RAV-1 envelope antigen; an infectious bronchitis virus antigen, e.g., a matrix antigen or a preplomer antigen; an infectious bursal disease virus antigen; a cholera antigen; a tumor associated antigen; a feline immunodeficiency virus antigen; a foot-and-mouth disease virus antigen; a Marek's Disease Virus antigen; a Staphylococci antigen; a Streptococci antigen; a *Haemophilus influenza* antigen, e.g., group b polysaccharide-protein conjugates; a papilloma virus; a poliovirus antigen; a rubella virus antigen; a poxvirus, such as smallpox antigen, e.g., vaccinia; a typhus virus antigen; a typhoid virus antigen; a tuberculosis virus antigen; an HTLV antigen; or, other bacteria, virus or pathogen antigen, such as a bacterial or viral surface antigen or coat protein. In one embodiment, the antigen is at least one polypeptide which includes an epitope that is recognized by cytotoxic T lymphocytes induced by an HIV polypeptide or derivative thereof. The polypeptide may be an HIV polypeptide or derivative thereof. HIV polypeptides may include HIV-1-gpl 20; HIV-1-gp 41; HIV-I-gp 160; HIV-1-pol; HIV-I-nef; HIV-I-tat; HIV-I-rev; HIV-I-vif; HIV-I-vpr; HIV-I-vpu; HIV-1-gag; HIV-2-gpl 20; HIV-2-gp 160; HIV-2-gp 41; HIV-2-gag; HIV-2-pol; HIV-2-nef; HIV-2-tat; HIV-2-rev; HIV-2-vif; HIV-2-vpr; HIV-2-vpu; and HIV-2-vpx.

TABLE 1 provides preferred antigens for the present invention.

| Antigen | Pathogen | Reference |
|---|---|---|
| Rabies glycoprotein G | Rabies | U.S. Pat. No. 5,830,477 |
| hemagglutinin protein (H), fusion protein (F), nucleoprotein (N) | Measles | U.S. 2011/0052627 |
| HSV-1 glycoproteins | Herpes simplex virus | U.S. Pat. No. 5,338,683<br>U.S. Pat. No. 6,183,750<br>U.S. Pat. No. 5,654,174 |
| hepatitis B surface antigen (HBsAg) | Hepatitis B virus | U.S. Pat. No. 7,045,313 |
| HCMV gB | Human cytomegalovirus | U.S. Pat. No. 5,338,683 |
| gp220, gp340, gH, gB | Epstein Barr Virus | U.S. Pat. No. 5,338,683,<br>U.S. Pat. No. 6,248,333 |
| hemagglutinin (InfHA), M2, M1, PB1 NP NAPB2 | Influenza | U.S. Pat. No. 5,676,950,<br>U.S. 2010/0143393<br>U.S. 2010/0204297 |
| NS1 | Dengue | U.S. Pat. No. 7,759,116 |
| NS1, prM, E | Yellow Fever | U.S. Pat. No. 5,744,140 |
| NS1, prM, NS2A | Japanese Encephalitis Virus | U.S. 10/497,633<br>U.S. Pat. No. 5,744,140 |
| E6 and E7 proteins | Human papilloma virus | U.S. Pat. No. 5,719,054 |
| F, HN proteins | Human parainfluenza virus | U.S. Pat. No. 6,811,784 |
| G protein | Vesicular stomatitis virus | U.S. Pat. No. 4,738,846 |
| LACK protein | Leishmania | U.S. 2010/0172933 |
| H, F proteins | Rinderpest | U.S. Pat. No. 5,003,058<br>U.S. Pat. No. 5,718,902 |
| gp13, gp14, gD, gp63, gE | Equine herpes virus | U.S. Pat. No. 5,482,713<br>U.S. Pat. No. 6,328,975 |
| gp50, gp63, gI, gII and gIII | Pseudorabies virus | U.S. Pat. No. 6,255,078<br>U.S. Pat. No. 6,183,750 |
| H7, H3, N7, N8 | Equine influenza virus | U.S. Pat. No. 4,920,213 |
| gp51, gp30, env | Bovine Leukemiavirus | U.S. Pat. No. 6,340,462 |
| E2 | Venezuenlan equine encephalomyelitis | U.S. Pat. No. 5,185,440<br>U.S. Pat. No. 6,936,257<br>U.S. Pat. No. 7,651,998 |
| HN, F, NP and M | Sendai virus | Sakaguchi et al. *J. Gen. Virol.* 74, 479-484, 1993 |
| H5 | Avian Influenza | U.S. 2011/0020391 |
| Vif, Vpr, Vpu, Vpx, Rev, Tat, Nef | HIV | U.S. Pat. No. 7,569,228 |
| TB10.4 | *Bacillus tuberculosis* | U.S. 2010/0015171 |
| OspC OspA | *spirochete Borrelia burgdorferi* | U.S. Pat. No. 6,872,550 |

In a preferred embodiment, the antigen is derived from *Bacillus anthracis*. When used herein, the term "*Bacillus anthracis*" or "*B. anthracis*" includes live and dead cells of Bacillus anthracis as well as spores. "Anthrax" when used herein means anthrax disease, i.e., the disease including the symptoms a subject experiences and/or suffers from when being infected with B. anthracis. B. anthracis antigenic determinants include, but are not limited to, the protective antigen (PA), edema factor (EF) and lethal factor (LF). For example, a preferred PA sequence comprises the amino acid sequence deposited in Genbank under AY428556.1 or AF268967.1. Variants of PA can also be used, such as the PA furin negative mutant sequence deposited as AY428556.1 and preferably, but not limited to, the codon-optimized sequence as shown in SEQ ID NO: 1 (nt 64-2277); its translation product is also shown in SEQ ID NO: 1 or in SEQ ID NO: 2. Both, EF and LF, are preferably modified to become inactivated.

Epitopes of PA, EF and LF are known in the field (See references in Table 2-4), for example, as disclosed by Yan et al. (2008), Vaccine 26(7): 947-55, and Abboud et al. (2009), J. Biol. Chem. 284(37): 25077-25086.

Table 2-4 provide examples of PA, EF and LF variants which are also applicable in the present invention. A skilled person is capable of generating PA variants using routine methods known in the art.

TABLE 2

Examples of PA variants

| | PA variants | Source |
|---|---|---|
| Truncated PA83 | AA 1-29 (secretion signal) of PA83 truncated | AA30-764 of NCBI accession number AF268967.1 |
| Rec-mutants | N682A and D683A | Chen et al. *J. Biol. Chem.* 2007; 282(13): 9834-45 |
| DNI mutants | K397D, D425K | Sellman et al. *Science* 2001; 292(5517): 695-7. |
| | F427D, F427N | Cao et al. *Infect. Immun.* 2009; (10): 4679-87 |
| | F427A, D425A, K563C | Janowiak et al. *Protein Science* 2009; 18: 348-358 |
| Oligo⁻ mutants | K199E, R468A, R470D, and D512K | Mogridge et al. *Proc Natl Acad Sci USA* 2002; 99(10): 7045-8 |
| SSSR mutants | R164S, K165S and K166S | Beauregard *Cell Microbiol* 2000; 2(3): 251-8 |
| $PA_{63}$ | PA processed from 83 to 63 kDa | Gordon et al. *Infect. Immun.*, 1995; 63(1): 82-7. |
| PA mutant | ΔD2L2 (deletion of residues 302-325) | U.S. Pat. No. 7,037,503 |
| cleavage site mutants | Furin cleavage site mutants (PA RKKR, PA RAAR, PA FTKR, PA STRR) | Gordon et al. *Infect. Immun.*, 1995; 63(1): 82-7. |
| | $PA_{CM}$ furin cleavage minus PA | Li et al. *Open Vaccine J.* 2009; 2: 92-99 |
| | PA83Δfurin (missing cleavage site RKKR) | Hermanson et al. *Proc. Natl. Acad. Sci. USA.* 2004; 101 (37): 13601-6, Genbank Accession No. AY428556.1 |
| recombinant PA | | U.S. Pat. No. 7,037,503 |
| PA mutants | PA-I (2β2-2β3 loop contains the residues of the amphipathic look of the homologous iota-b toxin) | SEQ ID NO: 1 in U.S. Pat No. 7,282,580 |
| PA47 | Truncated PA containing residues 315-735 furin cleavage site 164RKKR and chymotrypsin site 313 FF deleted His-Met at N-Terminal | U.S. Pat. No. 7,201,912 |
| PA variants | deletion of residues 162 through 167; substitution of isoleucine for Serine at residue 168; deletion of residues 304-317; and substitution of glycine for Serine at residue 319. | SEQ ID NO: 2 in U.S. Pat. No. 7,261,900 |
| PA mutants | Mutation at one or more residues 552, 574, 554, 562, 566, 425, 427, 346, 352, 350, 203, 205, 207, 226, 236. | U.S. 20050063986 |

TABLE 3

Examples of LF variants

| LF variants | | Source |
|---|---|---|
| $LF_{E687A}$ | E687A | Hammond et al. *Infect. Immun.*, 1998; 66(5): 2374-8 |
| truncated n-terminal LF fragment | LF domain 1, residues 10-254 truncated | Price et al. *Infect. Immun.* 2001; 69(7): 4509-15. |
| mutant LF | mLF-Y728A; E735A | Fasanella et al. *Vaccine* 2008; 26(45): 5684-8 |
| LF34-583 | Contains Domain I-III | AAR88322.1 |
| Δ27LFn | N-terminal 27 amino acids deletion of LFn (PA-binding domain of LF) | Kong et al. *FEBS Lett.* 2009; 583(8): 1257-60 |
| LF7 | substitution of Cys for E-687 | Klimpel et al. *Mol. Microbiol.*, 1994; 13(6): 1093-100. WO2005013898 |
| LF50 | C-terminal LF deletion mutant (401AA) | U.S. Pat No. 7,201,912 |
| LFE687C | Glu to Cys substitution in the zinc binding site | Duesbery et al., 1998; *Science* 280, 734-737. |

TABLE 3-continued

Examples of LF variants

| LF variants | | Source |
| --- | --- | --- |
| LF mutants | Mutation at one or more residues 137, 138, 140 and 142 | U.S. 20050063986 |

TABLE 4

Example of EF variants

| EF variants | | Source |
| --- | --- | --- |
| $EF_{H351A}$ | H351A | Gupta et al. Arch. Biochem. Biophys. 2006; 446(1): 28-34 |
| Non-functional mutant EF-K346R | K346R | Firoved et al. Am. J. Pathol. 2005; 167: 1309-20. |
| EFn | PA-binding domain of EF | Kong et al. FEBS Lett. 2009; 583(8): 1257-60; WO 2007011411 |
| EF mutants | Mutation at one or more residues 137, 138, 140 or 142 | U.S. 20050063986 |
| EF-S414N | S414N | Duverger et al. J. Immunol. 2010; 185: 5943-5952 |

Another example of an antigen is a smallpox protein. Smallpox is an infectious disease unique to humans, caused by either of two virus variants, Variola major and Variola minor. Vaccinia virus has been used as live vaccine to immunize against smallpox. Successful worldwide vaccination with vaccinia virus culminated in the eradication of variola virus. Known smallpox vaccines involve the use of smallpox antigens such as A33, B5 (Galmiche et al. (1999), Virol. 254: 71-80 and Fang et al. (2006), Virol. 345: 231-243), H3 (Davies et al. (2005), J. Virol. 79: 11724-11733), D8 (Sakhatskyy et al. (2006), Virol. 355: 164-174) and L1 (Hooper et al. (2000), Virol. 266: 329-339 and Hooper et al. (2003), Virol. 306: 181-195).

Thus, antigens in the present invention are not limited to heterologous genes. In the case of smallpox, the recombinant virus vector may already contain the antigen sequence in its genome. Thus, for the invention, the nucleic acid sequence encoding the TTC molecule may be inserted in the genome in such a way that the antigen sequence and the TTC are operably linked.

According to the present invention, the nucleic acid sequence encoding the antigen or antigenic epitope is operably linked to the tetanus toxin fragment C, TTC, coding sequence and/or an epitope, fragment, variant and/or equivalent thereof. Thus, as already indicated above, the term "TTC coding sequence" as used herein encompasses the sequence for the full-length TTC molecule and/or antigen and/or epitope thereof and/or the sequence of any other TTC molecule/variant/equivalent giving rise to the surprising result of immune response enhancement as described further above. The full-length fragment C is located at the C-terminus (aa 865-1315) of tetanus toxin (deposited in Genbank under Accession Number NP_783831.1).

Accordingly, in a preferred embodiment of the recombinant poxvirus vector described herein, the nucleic acid encoding the tetanus toxin fragment C comprises amino acids 865-1315 of tetanus toxin, more preferably tetanus toxin fragment C comprises amino acids 947-967 of tetanus toxin or amino acids 1273-1284 of tetanus toxin.

Also, in a preferred embodiment of the recombinant poxvirus vector described herein, the nucleic acid encoding the tetanus toxin fragment C comprises nucleotides 2281-3642 of SEQ ID NO: 1.

TTC is believed to act as immunostimulant for the antigen and/or antigenic epitope expressed by the same vector. Preferably, the two sequences are fused together as fusion protein, with or without linker peptide in between. Alternatively, the sequences can be translationally coupled together. The inventors have indeed found that the TTC expressed by poxvirus is capable of enhancing an earlier antibody production to protective antigen. In particular, the inventors have observed 100% seroconversion after just one immunization of the poxvirus, compared to constructs without the TTC (FIGS. 1-4).

The TTC sequence encodes preferably the amino acid sequence of Genbank Accession No. ACR19198.1. A TTC sequence is defined herein as a sequence having at least about 50%, 60%, 65% 70%, 75%, 80%, 81%, 82%, 83%, 84%, 85%, 86%, 87%, 88%, or 89%, more typically at least about 90%, 91%, 92%, 93%, or 94% and even more typically at least about 95%, 96%, 97%, 98% or 99%, most typically at least about 99% amino acid identity with the sequence of Genbank Accession No. ACR19198.1. An example is the sequence of Genbank Accession NO. AAF73267.1 (98% identity using Blosum 62 matrix and gap weight of 2 and a length weight of 4).

Preferably, the sequence is codon optimized for expression in human. A preferred TTC nucleic acid sequence is shown in SEQ ID NO: 1 (nt 2281-3642), its translation product is also shown in SEQ ID NO: 2.

For the purpose of the present invention, epitopes of tetanus toxin fragment C or fragments of TTC containing an epitope of TTC can be incorporated in the poxvirus vector. Tetanus toxin fragment C has two T-cell epitopes. P30 (SEQ ID NO: 4) FNNFTVSFWLRVPKVSASHLE is located at positions 947-967 of the tetanus toxin. (Demontz et al. (1989), J. Immunol. 142(2): 394-402; WO 96/34888; WO 95/31480; WO 95/26365). The FNNFTV sequence may optionally be deleted.

Another T cell epitope is P4 (SEQ ID NO: 5) GQIGND-PNRDIL corresponding to positions 1273-1284 of TTC (Panina-Bordignon et al (1989), Eur. J. Immunol. 19: 2237-2242). A further T cell epitope comprises P21 IREDNNITL (SEQ ID NO: 6) which corresponds to positions 1064-1072 of the tetanus toxoid and contain the sequence as disclosed in WO 97/10335.

Further T cell epitopes are described in US 2007/0003566, including P23 VSIDKFRIFCKANPK (SEQ ID NO: 7), corresponding to AA positions 1084-1099 of TT, and P32 LKFIIKRYTPNNEIDS (SEQ ID NO: 8), corresponding to AA positions 1174-119.

Epitopes of TTC includes variants of the epitopes described above. Hence, a TTC epitope has a sequence at least about 80%, 81%, 82%, 83%, 84%, 85%, 86%, 87%, 88%, or 89%, more typically at least about 90%, 91%, 92%, 93%, or 94% and even more typically at least about 95%, 96%, 97%, 98% or 99%, most typically at least about 99% amino acid identity with any of SEQ ID NO: 4-8. Preferably, the sequence is codon optimized for expression in human.

In a preferred embodiment of the present invention, the recombinant poxvirus vector comprises a promoter sequence regulating the expression of the protein comprising the TTC molecule, said TTC molecule being operably linked to an antigen and/or an epitope thereof.

Accordingly, the poxvirus vector contains preferably at least one promoter sequence which regulates the expression of the antigenic determinant and/or the TTC molecule and/or antigen and/or epitope thereof. For the purpose of the present invention, viral promoters are preferred for the expression of antigen genes, because poxviruses replicate in the cytoplasm and have their own transcriptional system. Poxvirus promoters encompass mainly three varieties (early, intermediate, and late) and various strengths. Early promoters drive expression before viral DNA replication, whereas intermediate and late promoters drive expression successively after DNA replication. Suitable promoters include the 30K and 40K promoters (U.S. Pat. No. 5,747,324), a strong synthetic early/late promoter (see Sutter et al. (1994), Vaccine 12: 1032-40,), the p7.5 promoter (Endo et al. (1991), J. Gen. Virol. 72: 699-703,) and the promoter derived from the cowpox virus A-type inclusion (ATI) gene (WO 2004084582). Other promoters such as MVA promoters (EP 1 536 015), synthetic early/late promoter PrS or the late promoter PrSSL (WO 2010/060632), as well as the poxvirus early/late hybrid promoter promoters (WO 2010/102822) may also be used. Early promoters are capable of strong expression at early time points after infection and thus effect that a desired antigen is presented via MHC I. An early/late promoter drives expression of a linked nucleic acid sequence at both early and late times of the viral lifecycle. The promoters mentioned above are examples of generally used promoters, as other promoters known to a skilled artisan are also encompassed in the present invention.

The recombinant poxvirus may further comprise marker and/or selection genes operably linked to the promoter. Selection genes are known to a skilled person in the art, for example, 13-Galactosidase, neomycin, phosphoribosyltransferase, the *E. Coli* GPT gene (Falkner et al. (1988), J. Virol. 62(6): 1849-1854,) and monomeric red fluorescent protein (mRFP1) gene may be used. Other marker genes such as neomycin phosphotransferase gene (NPTII) and enhanced Green Fluorescent Protein (eGFP) (as described in the examples) are also suitable. The use of selection or marker cassettes simplifies the identification and isolation of the generated recombinant poxvirus. A modified procedure uses both GPT and 3-gal for transient selection (Carroll et al. (1997), Curr Opin Biotechnol. 8(5): 573-7,). Nevertheless, a recombinant poxvirus can also be identified by PCR technology.

In another preferred embodiment, the recombinant poxvirus vector of the present invention comprises a nucleic acid encoding a leader peptide. The leader peptide may precede TTC or may precede the antigenic determinant.

As used herein, the term leader peptide refers to any signal sequence that directs the synthesized antigen protein away from the translation site, including signaling sequences or secretory sequences that lead the antigen peptide to the cell membrane. The leader peptide may be a naturally occurring sequence or a synthetic sequence. In one embodiment, the leader peptide is the SecTag or SecTag2 (Ig kappa-chain leader sequence). The SecTag is, for example, shown in SEQ ID NO: 1 (nt 1-63). A skilled person may readily identify suitable leader peptide sequence for use in the present application.

In the present invention, the antigen sequence may preferably be operably linked to a membrane anchor sequence so that the translated antigens can be targeted to the cell surface. A membrane anchor refers to any polypeptide (including a glycosylated polypeptide) capable of anchoring heterologous polypeptides to the outer face of the cell membrane. Preferably, the membrane anchor comprises the cytoplasmic and transmembrane domains of Vaccinia virus B5R protein, termed herein as the "B5R anchor." As defined, a B5R anchor refers to the 42-amino-acid C-terminal segment of the B5R protein from any type of Vaccinia virus, for example, the WR strain (Katz et al. J. Virol. 71(4):3178-87), or more preferably an MVA. In addition, B5R anchor variants having at least 80%, such as at least 85%, for example at least 90%, or at least 95%, such as at least 98% sequence identity with respect to the reference B5R anchor sequence are also included in the present invention. A preferred anchor sequence is shown in SEQ ID NO: 3.

In other preferred embodiments, the recombinant poxvirus vectors may further comprise nucleic acids encoding one or more co-stimulatory molecules. The initiation of an immune response requires at least two signals for the activation of naive T cells by antigen presenting cells (APCs). The first signal is antigen specific, delivered through the T-cell receptor via the peptide/major histocompatibility complex, and causes the T cell to enter the cell cycle. The second, or the "co-stimulatory," signal is required for cytokine production and proliferation. The term "co-stimulatory molecule" is defined herein as a molecule which interacts with a T cell which has received a primary activation signal to result in T cell proliferation and/or cytokine production. Preferred co-stimulatory molecules include antigens on the surface of B lymphocytes, professional antigen presenting cells (e.g., monocytes, dendritic cells, Langerhans cells) and other cells which present antigen to immune cells (e.g., keratinocytes, endothelial cells, astrocytes, fibroblasts, oligodendrocytes). Co-stimulatory molecules such as IL12, IL-15 (US 20060147419) or parts thereof, such as IL15 Ra-sushi domain (US 20090238791), CD-70 (U.S. Pat. No. 7,906,638 or US 20100215674) and TRICOM®, which consists of B7.1, ICAM-1 and LFA-3 (US 20040101522, Hodge et al. (1999), Cancer Res. 59: 5800; Marshall et al. (2005), J Clin Oncol. 23(4): 720-731) can be employed. A skilled person in the art is capable of producing such constructs with standard techniques known, for example as described in the above references. Preferred co-stimulatory molecules in the present invention are, in particular, CD70, IL-12 and/or IL-15.

The nucleic acid sequence encoding a protein comprising the TTC molecule operably linked to an antigenic determinant/antigen/epitope may be inserted into a non-essential region of the poxvirus genome. Non-essential segments of the poxvirus genome are known to those skilled in the art. A skilled artisan can also readily identify such regions in the poxvirus by, for example, testing segments of virus DNA for regions that allow recombinant formation without affecting virus viability of the recombinant. One suitable region that is present in many poxviruses is the thymidine kinase (TK) gene.

In fowlpox, in addition to the TK region, other insertion regions include, for example, BamHI J (Jenkins, et al. (1991), Retroviruses 7: 991-998,) the EcoRI-HindIII fragment, BamHI fragment, EcoRV-HindIII fragment, BamHI fragment and the HindIII fragment set forth in EP 0 308 220. In swinepox preferred insertion sites include the thymidine kinase gene region and the HindIIIC region. In vaccinia, in addition to the TK region, other insertion regions include, for example, HindIII M. For MVA virus genome, the antigen may be inserted into a host range gene or at a naturally occurring deletion site (WO 97/02355), or for example, into an intergenic region (IGR) of the MVA genome (WO 03/097845), in particular, into intergenic regions IGR07/08, IGR 44/45, or more preferably IGR64/65, IGR88/89 or IGR148/149. Genes encoding different antigens can be inserted into the same or different insertion sites.

It is preferred that the recombinant poxvirus of the present invention is suitable (or is for use or is for use in a method) for affecting an immune response in a subject.

Also, in a further aspect, the invention provides a method for affecting an immune response in a subject by administering the recombinant poxvirus vector described herein to a subject. In the context of the present invention, the term "subject" encompasses any suitable animal species, in particular a vertebrate animal. Preferred are mammals such as sheep, horses, swine, raccoon, dogs, cats, rabbits, rats, mice and cattle, camels, herbivores and humans, with humans being preferred. Further specific examples for animals are pets including dogs, cats as well as economically important animals such as calves, cattle, sheep, goats, horses, pigs. Other animals such as mice and rats are also encompassed. Additionally, the present invention may also be used for economically important birds such as turkeys, ducks, goose, raptors and hens.

The term "immune response" refers to a reaction of the immune system to an antigenic molecule in the body of a host, which includes generation of an antigen-specific antibody and/or cellular response including a cytotoxic immune response. More specifically, an "immune response" to an antigen or vaccine composition is the development of a humoral and/or a cell-mediated immune response. For purposes of the present invention, a "humoral immune response" is an antibody-mediated immune response and involves the generation of antibodies with affinity for the antigen/vaccine of the invention, while a "cell-mediated immune response" is one mediated by T-lymphocytes and/or other white blood cells. A "cell-mediated immune response" is elicited by the presentation of antigenic epitopes in association with Class I or Class II molecules of the major histocompatibility complex (MHC). A "cell-mediated immune response" also refers to the production of cytokines, chemokines and other such molecules produced by activated T-cells and/or other white blood cells, including those derived from CD4+ and CD8+ T-cells.

The "immune response" can preferably be a "protective" immune response, however it is not necessary that the immune response is protective, since it may also be beneficial if the spread of an infectious disease is decreased or blocked in a population. A "protective" immune response refers to the ability of a vaccine to elicit an immune response, either humoral or cell mediated or both, which serves to protect the mammal from an infection. The protection provided need not be absolute, i.e., the infection need not be totally prevented or eradicated, if there is a statistically significant improvement compared with a control population of mammals. Protection may be limited to mitigating the severity or rapidity of onset of symptoms of the infection.

Effective dosages of the present invention for affecting the immune response vary depending upon many different factors, including the type of antigen, means of administration, target site, whether the subject is human or an animal, and whether treatment is prophylactic or therapeutic. Preferably, a dosage of the recombinant poxvirus of $10^6$ to $10^9$ $TCID_{50}$ is administered to the subject. More preferably, a dosage of $10^6$ to $5\times10^9$ $TCID_{50}$ is administered to the subject. Most preferably, a dosage of $10^7$ to $10^9$ $TCID_{50}$ is administered to the subject.

Administration can be done by any route of administration as determined by a skilled person. Preferably, administration is intramuscular, intravenous, subcutaneous (e.g., by scratching or injection), nasal (e.g., by inhalation) or oral.

The inventors have found that the recombinant poxvirus vector of the present invention is capable of eliciting/inducing an early seroconversion in the subject. As used herein, "seroconversion" refers to the development of antibodies to a particular antigen or antigenic epitope. Preferably, the seroconversion is 100% after, e.g., 2, 3, 5, 7, 10, 14, 20, 21, 24, 36, 40, 49, 50 days. Thus, in a further embodiment the recombinant poxvirus of the invention is suitable (or is for use or is for use in a method) for early enhancing the antibody titer against an antigenic determinant.

In another aspect, the present invention provides a composition comprising the recombinant poxvirus vector. Processes for preparing poxvirus containing compositions suitable as, e.g., vaccines or as a medicament are known to the person skilled in the art (see, for example, Joklik W. K. (1962), Virology 18: 9-18; Richter, K. H. (1970), Abhandlungen aus dem Bundesgesundheitsamt 9: 53-57). Preferably, the poxvirus composition is prepared in freeze-dried form. A freeze-dried product can be stored at temperatures in the range from 4° C. to 25° C.

Processes for the freeze-drying of poxviruses, vaccinia virus in particular, and virus containing compositions and solutions suitable for this purpose are known (Burke et al. (1999), Critical Reviews in Therapeutic Drug Carrier Systems 16: 1-83,).

Another aspect of the present invention concerns the recombinant poxvirus as described herein for use as a medicament (or pharmaceutical composition) or vaccine. The composition may be used, for example, against infectious diseases, but may also be employed, e.g., against tumor/cancer diseases.

Preferably, an immunogenic amount of the recombinant poxvirus vector is comprised in the medicament or vaccine. The medicament or vaccine is, in various embodiments, useful for treating or vaccinating against a targeted pathological condition or a disease. The term "vaccinating" includes treatment and/or prevention of a pathological condition. U.S. Pat. No. 7,094,412 teaches how to use prepared poxviruses to manufacture a vaccine. The description is incorporated herein in its entirety.

As already mentioned, the "vaccine" can be used to prevent or treat a pathological condition in a subject. The term encompasses both subunit vaccines, i.e. vaccine compositions containing antigens which are separate and discrete from a whole organism with which the antigen is associated in nature, as well as compositions containing the recombinant poxvirus of the present invention carrying, inter alia, the antigen and/or an epitope thereof. The vaccine may or may not include one or more additional components that enhance the immunological activity of the active component. A vaccine may additionally comprise further components typical to pharmaceutical compositions. The vaccine of the present invention is, preferably, for human and/or veterinary use.

The vaccine or the composition comprising the pox virus may generally include one or more pharmaceutically acceptable carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules, such as proteins, polysaccharides, polylactic acids, polyglycolic acids, polymeric amino acids, amino acid copolymers, lipid aggregates, or the like.

The pharmaceutical composition or vaccine according to the present invention may comprise an adjuvant. As used herein, an "adjuvant" refers to a substance that enhances, augments or potentiates the host's immune response (antibody and/or cell-mediated) to an antigen or fragment thereof. A typical adjuvant may be aluminium salts, such as aluminium hydroxide or phosphate, Quil A, bacterial cell wall peptidoglycans, virus-like particles, polysaccharides, toll-like receptors, nano-beads, etc. (Aguilar et al. (2007), Vaccine 25: 3752-3762,).

The recombinant poxvirus vector in the present invention can be advantageously used to manufacture a medicament or vaccine which is useful for treating and/or preventing a pathological condition such as an infectious disease or a tumor/cancer disease.

For example, when the targeted pathological condition is anthrax, the vector may be engineered to express protective antigen (PA), edema factor (EF), lethal factor (LF), or an epitope of one or more of these antigens, or a variant of one or more of said antigens, fused to TTC, as described in the Examples.

When the targeted pathological condition is dengue fever, the antigen can be selected from dengue antigens such as preM, E, NS1 antigens originating from dengue virus type 1, 2, 3 or 4.

For the preparation of vaccines, the recombinant poxvirus according to the invention may be converted into a physiologically acceptable form. This can be done based on the experience in the preparation of poxvirus for the vaccination against smallpox (Stickl et al. (1974), Prev. Med. 3(1): 97-101,).

For example, the purified poxvirus can be stored at −80° C. with a titer of $5 \times 10^8$ or $10^9 TCID_{50}$/ml formulated in about 10 mM Tris, 140 mM NaCl pH 7.4. For the preparation of vaccine shots, e.g., $10^2$-$10^8$ or $5 \times 10^8$ or −$10^9$ particles of the virus can be lyophilized in 1-100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g. human serum albumin) suitable for in vivo administration. The glass ampoule may then be sealed and stored between 4° C. and room temperature for several months, most preferably at temperatures below −20° C.

For vaccination or therapy, the lyophilisate can be dissolved in an aqueous solution, preferably physiological saline or Tris buffer, and administered either systemically or locally, i.e. parenteral, subcutaneous, intravenous, intramuscular, or any other path of administration known to the skilled practitioner. The mode of administration, the dose and the number of administrations can be optimized by those skilled in the art in a known manner. However, most commonly, a patient is vaccinated with a second shot about one month to six weeks after the first vaccination shot.

In a preferred embodiment, the administration of the recombinant poxvirus vector affects the T cell response of the subject. The T cell response to said at least one antigen and/or antigenic epitope may be induced by heterologous prime-boost regimes in which one or more of the vaccinations is done with a virus as defined above and in which one or more of the vaccinations is done with another type of vaccine, e.g. another virus vaccine, a protein or a nucleic acid vaccine. However, preferably, said T cell response is induced by homologous prime/boost regimes in which the same or a related replication deficient recombinant virus is used for both prime and boost vaccinations.

Accordingly, in another preferred embodiment, said T cell response may be induced by an immunization regimen comprising homologous prime/boost administrations. In further embodiments said T cell response is induced by an immunization regimen comprising at least three or at least four or even further administrations of the replication deficient recombinant virus or the pharmaceutical composition or vaccine as defined above.

The present invention also encompasses a kit comprising at least two vials for prime/boost immunization comprising the recombinant poxvirus as described herein for a first inoculation ("priming inoculation") in a first vial/container and for an at least second and/or third and/or further inoculation ("boosting inoculation") in a second and/or further vial/container. The kit may comprise at least one, two, three, four, or more containers or vials of the recombinant virus, together with instructions for the administration of the virus to a subject.

In a preferred embodiment, the subject is a human. The instructions may indicate that the recombinant virus is administered to the subject in multiple (i.e., 2, 3, 4, 5, 6, etc.) dosages at specific time points (e.g., at least 4 weeks, at least 6 weeks, at least 8 weeks after the previous administration). Preferably, the instructions indicate that the recombinant virus is to be administered in at least 3 or at least 4 dosages.

In one embodiment, the first dosage comprises $10^7$ to $10^9$ $TCID_{50}$ of the recombinant poxvirus and the second dosage comprises $10^7$ to $10^9$ $TCID_{50}$ of the virus. In another embodiment, the third and/or fourth and/or further dosage comprises $10^7$ to $10^9$ $TCID_{50}$ of the virus. As used herein, a "booster" or "boosting" refers to a further or later vaccine dose given after the primary dose(s) to increase the immune response to the original vaccine antigen(s). The vaccine given as the booster dose may or may not be the same as the primary vaccine.

Given the above, the recombinant poxvirus can be contained in one or multiple vials or containers, together with instructions for the administration of the virus. The instructions can indicate that the recombinant poxvirus is administered to the subject in a single dosage, or in multiple (i.e., 2, 3, 4, etc.) dosages. The instructions can indicate that the poxvirus is administered in a first (priming) and second (boosting) administration.

The concentration of the vaccine can be determined by a skilled person using routine techniques. For example, it may be in the range of $10^4$ to $10^9$ $TCID_{50}$/ml, (tissue culture infectious dose), for example in the range of $10^5$ to $5 \times 10^8$ $TCID_{50}$/ml, such as in the range of $10^6$ to $10^8$ $TCID_{50}$/ml or $10^7$ to $10^8$ $TCID_{50}$/ml. Preferably, the concentration is in the range of $10^7$ to $10^8$ $TCID_{50}$/ml. The vaccination dose for human may be in the range of $10^8$ to $10^9$ $TCID_{50}$/ml. A preferred dose for humans comprises between $10^6$ to $10^9$ $TCID_{50}$, including a dose of $10^6$ $TCID_{50}$, $10^7$ $TCID_{50}$, $10^8$ $TCID_{50}$ or $5 \times 10^8$ $TCID_{50}$.

Administration is done at least once, preferably twice, three times, four times, five times, six times or even more times.

Given the immunostimulating property of TTC, the present invention also provides a method of initiating or enhancing an immune response to an antigen in a subject. The method comprises administering to the subject a recombinant poxvirus vector expressing the antigenic determinant being operably linked to a tetanus toxin fragment C. The poxvirus can be administered either systemically or locally, i.e. parenteral, subcutaneous, intravenous, intramuscular, or any other path of administration known to the skilled practitioner.

Furthermore, the present invention provides a recombinant poxvirus as described herein for the treatment and/or prevention of a pathological condition in a subject. The pathological condition is preferably a disease caused by a bacterium, fungus, virus, prion, unicellular organism or parasite, but does also encompass, e.g., tumor/cancer diseases. Antigen(s) or antigenic epitope(s) to be cloned and expressed by the poxvirus vector depend(s) on the pathological condition to be treated or prevented. As used herein, the term "treating" or "preventing" means to at least partially inhibit growth of, to partially inhibit the transmission, to partially prevent the pathogen from establishing itself in a subject, and/or to ameliorate or alleviate the symptoms of the disease caused by the pathogen. In one preferred embodiment, the condition is caused by *Bacillus anthracis* or Dengue virus.

In preferred embodiments, the treatment comprises at least three, four, five or even more administrations (corresponding to a first prime followed by at least two, three, four, five or even more boost administrations) of the recombinant poxvirus vector, preferably a recombinant MVA to the host. Administration of the recombinant virus may be accomplished by prime-boost administration, i.e., said at least three administrations comprising a first inoculation (prime inoculation/immunization) followed by a second, third or further inoculation (boosting inoculations/immunizations).

In a further aspect, the present invention provides a (host) cell comprising the recombinant poxvirus vector described herein. Examples of cells that are permissive to poxviruses include, but are not limited to, COS, HEK-293, BHK, CHO, TM4, CVI, VERO-76, HELA, MDCK, BRL 3A and NIH/3T3 cells. For MVA, the preferred cells are CEF and BHK cells. Additional cell lines are known to those of ordinary skill in the art. Introduction of the poxvirus construct into a cell can be effected by calcium phosphate transfection, electroporation, infection, and other methods known in the art and described in standard laboratory manuals, such as *Current Protocols in Molecular Biology* John Wiley & Sons, Inc. New York.

In another aspect, the present invention provides (host) cells infected with the recombinant poxvirus. According to this aspect, the (host) cell can be infected with a poxvirus, preferably with an MVA viral vector, and transfected with a further vector, e.g., plasmid vector, comprising the gene to be inserted, preferably under the transcriptional control of an MVA or poxvirus expression control element or promoter, such as the synthetic PrS promoter. As explained above, the plasmid vector comprises sequences capable of directing the insertion of the heterologous sequence into a selected part of the poxvirus genome, such as those flanking one of the naturally occurring deletion sites or intergenic regions.

In another aspect, the invention also provides a method of generating a recombinant poxvirus. Generation of recombinant poxvirus can be carried out by methods described in the following references: *Virology Methods Manual*, edited by Brian W J Mahy and Hillar O Kangro. Academic Press., 1996, describes techniques for the handling and manipulation of viruses; *Molecular Virology: A Practical Approach*, edited by A J Davison and R M Elliott; The Practical Approach Series, IRL Press at Oxford University Press. Oxford, 1993. Chapter 9: Expression of genes by Vaccinia virus vectors; *Current Protocols in Molecular Biology*, Publisher: John Wiley and Son Inc., 1998. Chapter 16, section IV: Expression of proteins in mammalian cells using Vaccinia viral vector, which describes techniques and know-how for the handling, manipulation and genetic engineering of poxvirus and particularly vaccinia virus.

In addition, suitable methods are also described by Piccini et al. in *Methods of Enzymology*, 1987; 153: 545-563; U.S. Pat. Nos. 4,769,330; 4,722,848; 4,769,330; 4,603,112; 5,110,587; 5,174,993; EP 83286; EP 206920; Mayr et al. (1975), Infection 3: 6-14; Sutter and Moss (1992), Proc. Natl. Acad. Sci. USA 89: 10847-10851.

The nucleic acid sequence to be inserted can be placed into a suitable plasmid or vector, such as an *E. coli* plasmid construct, where DNA homologous to a section of poxvirus genome, has been inserted. The DNA sequence is for example flanked on one or both ends by sequence homologous to the DNA sequence flanking a region of poxvirus insertion site. Then, the resulting plasmid construct can be amplified by growth within *E. coli* bacteria and isolated. The isolated plasmid containing the DNA gene sequence to be inserted can be transfected into a cell culture, e.g., chicken embryo fibroblasts (CEF) infected with the poxvirus. Recombination between homologous poxvirus DNA in the plasmid and the viral genome can then take place in the infected cells.

In a preferred embodiment, the method comprises
1) infecting a host cell with a pox virus,
2) transfecting the infected cell with a recombinant vector comprising a tetanus toxin fragment C (TTC) coding sequence, said TTC coding sequence being operably linked to an antigenic determinant, in particular to a bacterial antigenic determinant, said vector further comprising a genomic pox virus sequence capable of directing the integration of the TTC and antigenic determinant coding sequences into the poxvirus genome, and
3) identifying, isolating and, optionally, purifying the generated recombinant poxvirus.

Given the above method of generating a recombinant poxvirus, the present invention also provides a recombinant poxvirus generated or producible (i.e. obtained or being obtainable) by said method.

In another aspect, the present invention provides a method of producing the recombinant pox virus according to the present invention and/or an antigenic determinant and TTC molecule using the recombinant poxvirus vector described herein. The antigenic determinants may be any antigens and/or epitopes thereof as described earlier, such as polypeptides obtained from bacteria, fungus, virus, prion, unicellular organism or parasite. The antigen can be useful for the formulation of subunit vaccine. "Subunit vaccine" refers to a type of vaccine that includes one or more antigens prepared from at least partially purified, or substantially purified, immunogenic polypeptides from one or more target pathogen. The vaccine composition is substantially free of intact pathogen cells or pathogenic particles, or the lysate of such cells or particles. The TTC expressed at the same time by the poxvirus vector would advantageously enhance the immunogenicity of the antigen or epitope and thereby improve the immune response to the antigen or epitope in the subject.

For the purpose of the present invention, the method comprises the steps of
1) infecting a host cell with the recombinant poxvirus provided in the present invention or, alternatively, transfecting the cell with the DNA of such recombinant poxvirus,
2) cultivating the infected or transfected cell, and
3) isolating the pox virus, the antigenic determinant and TTC molecule expressed from said recombinant poxvirus vector from said cell.

A skilled person can readily select cells that are suitable for the propagation of poxviruses, such as COS, HEK-293, BHK, CHO, TM4, CVI, VERO-76, HELA, MDCK, BRL 3A, NIH/3T3, CEF or BHK cells. Further details for the method can be found in EP 206920 and EP 206939, incorporated herein by reference, as well as in the Examples.

Of course, the present invention also includes recombinant poxvirus, antigenic determinant(s) as well as TTC molecules produced or producible (i.e. obtained or being obtainable) by said method.

For avipoxviruses, since they replicate only in avian cells, avian cells generally have to be used for their amplification.

The present invention can also be characterized by the following items:

1. A recombinant poxvirus comprising a a tetanus toxin fragment C (TTC) coding sequence, said TTC coding sequence being operably linked to a bacterial antigenic determinant coding sequence.
2. The recombinant poxvirus according to item 1, wherein said poxvirus is attenuated.
3. The recombinant poxvirus according to item 1 or 2, wherein the poxvirus is a vaccinia virus.
4. The recombinant poxvirus according to item 3, wherein the vaccinia virus is a Modified Vaccinia Virus Ankara (MVA).
5. The recombinant poxvirus according to item 4, wherein the MVA used for generating the recombinant virus is an MVA-BN virus having the capability of reproductive replication in vitro in chicken embryo fibroblasts (CEF) cells, but no capability of reproductive replication in the human keratinocyte cell line HaCat, the human bone osteosarcoma cell line 143B, the human embryo kidney cell line 293, and the human cervix adenocarcinoma cell line HeLa.
6. The recombinant poxvirus according to item 4 or 5, wherein the MVA is MVA-BN as deposited at the European Collection of Animal Cell cultures (ECACC) under number V00083008.
7. The recombinant poxvirus according to any of the preceding items, wherein the tetanus toxin fragment C coding sequence encodes amino acids 865-1315 of tetanus toxin.
8. The recombinant poxvirus according to item 7 wherein the tetanus toxin fragment C coding sequence encodes amino acids 947-967 of tetanus toxin.
9. The recombinant poxvirus according to item 7 wherein the tetanus toxin fragment C coding sequence encodes amino acids 1273-1284 of tetanus toxin.
10. The recombinant poxvirus according to item 7, wherein the tetanus toxin fragment C coding sequence comprises nucleotides 2281-3642 of SEQ ID NO: 1.
11. The recombinant poxvirus according to any of the preceding items comprising a further antigenic determinant coding sequence being operably linked to the TTC coding sequence.
12. The recombinant poxvirus according to any of the preceding items, wherein the antigenic determinant coding sequence is a *Bacillus anthracis* antigenic determinant coding sequence.
13. The recombinant poxvirus of item 12, wherein the antigenic determinant coding sequence is selected from one or more elements of the group consisting of protective antigen (PA), lethal factor (LF), edema factor (EF) antigenic determinant coding sequence.
14. The recombinant poxvirus of item 13, wherein the antigenic determinant coding sequence is PA antigenic determinant coding sequence.
15. The recombinant poxvirus according to any of the preceding items comprising a nucleic acid encoding a co-stimulatory molecule.
16. The recombinant poxvirus of item 15, wherein the co-stimulatory molecule is CD70, IL-12 and/or IL-15.
17. The recombinant poxvirus according to any of the preceding items for use in affecting an immune response in a subject.
18. The recombinant poxvirus according to any one of items 1-17 for use in increasing the antibody titer against an antigenic determinant.
19. The recombinant poxvirus according to any of the preceding items for use as medicament or vaccine.
20. The recombinant poxvirus according to any one of items 12 to 19 for use as medicament or vaccine for the treatment and/or prevention of anthrax.
21. A composition comprising the recombinant recombinant poxvirus according to any one of items 1-20.
22. A vaccine comprising the recombinant poxvirus according to any one of items 1-20.
23. A cell comprising the recombinant poxvirus according to any one of items 1-20.
24. Use of the recombinant poxvirus according to any one of items 1-20 for the manufacture of a medicament or vaccine.
25. The use according to item 24 for the manufacture of a medicament or vaccine for treating and/or preventing a pathological condition.
26. A method for affecting an immune response to an antigenic determinant in a subject, the method comprising administering to the subject a recombinant poxvirus according to any one of items 1-20.
27. The recombinant poxvirus according to any one of items 17-20, the use according to item 24 or 25 and/or the method according to item 26, wherein the recombinant poxvirus is or is to be administered once, twice, three times or four times.
28. A method of generating a recombinant poxvirus according to any one of items 1-20, comprising the steps of
    1) infecting a host cell with a poxvirus,
    2) transfecting the infected cell with a recombinant vector comprising a tetanus toxin fragment C (TTC) coding sequence, said TTC coding sequence being operably linked to a bacterial antigenic determinant coding sequence, said vector further comprising a genomic poxvirus sequence capable of directing the integration of the TTC and antigenic determinant coding sequences into the poxvirus genome, and
    3) identifying, isolating and, optionally, purifying the generated recombinant poxvirus.
29. A recombinant poxvirus generated according to the method of item 28.
30. A method for producing a recombinant poxvirus according to any one of items 1-20 and/or the antigenic determinant and TTC molecule expressed from the genome of said recombinant poxvirus vector, comprising the steps of
    infecting a host cell with the recombinant poxvirus of any one of items 1-20 or transfecting the cell with the recombinant DNA of the recombinant poxvirus,
    cultivating the infected or transfected cell,
    isolating the poxvirus and/or the antigenic determinant and TTC molecule from said cell.
31. A recombinant poxvirus and/or an antigenic determinant and TTC molecule obtained from the method according to item 30.
32. A kit comprising the recombinant poxvirus according to any one of items 1-20, 29 and/or 31 in a first vial or container for a first administration (priming) and in a second vial or container for a second administration (boosting).

33. The kit of item 32, comprising in a third, fourth or further vial or container the recombinant poxvirus for a third, fourth or further administration (boosting).

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, and temperature is in degrees Celsius. Standard abbreviations are used.

Example 1

Recombinant Poxvirus Vector Comprising PA-TTC Sequence

A recombinant plasmid containing the sequence for a PA or PA variant, such as PA83, PA63, PA47, PA furin negative or other PA mutants (such as described in Table 2), along with a promoter sequence. For integration into the genome of modified vaccinia virus Ankara suitable flanking sequences are, e.g., DNA sequences adjacent to the intergenic region IGR 64/65 or IGR 148/149 that can be introduced in a suitable vector. For an improved secretion of expressed antigens, vectors can include appropriate leader sequences that encode secretion signals. For example, a suitable vector could be the pSecTag2 vectors (Invitrogen, Carlsbad, Calif., USA), containing a 21 AA amino-terminal secretion sequence SecTag2 from the V-J2-C region of the mouse Ig kappa-chain (METDTLLLWVLLLWVPGSTGD; see SEQ ID No:1 or 2) which can be used for an efficient secretion of recombinant proteins. The sequence is N-terminally fused to the antigen sequence (see Examples 2-4). Additional codon optimization can be carried out to avoid homologous recombination between identical DNA sequences of SecTag2 if used several times in one recombinant poxvirus. For example, the codon can be optimized in the following way:

```
                                            (SEQ ID NO: 9)
I:   ATGGAGACCG ACACCCTGCT GCTGTGGGTC CTGCTCCTGT

GGGTGCCCGG CAGCACCGGC GAC
                                            (SEQ ID NO: 10)
II:  ATGGAAACAG ATACACTCCT CCTCTGGGTG CTCCTGCTCT

GGGTCCCAGG ATCCACAGGG GAT
                                            (SEQ ID NO: 11
III: ATGGAAACCG ACACTCTCCT GTTATGGGTT TTGCTTCTTT

GGGTTCCCGG AAGTACTGGC GAT
                                            ((SEQ ID NO: 12)
IV:  ATGGAAACTG ATACTCTGCT TCTGTGGGTG CTGCTGCTCT

GGGTCCCTGG GAGCACAGGT GAC
```

Nucleotide 64-2271 of SEQ ID NO: 1 corresponds to the PA83 sequence after codon optimization.

Host cells are infected with a poxvirus and subsequently with the recombinant plasmid mentioned above. For further selection and isolation, techniques as exemplified in Example 2-4 are used.

Example 2

Construction of MVA PA-TTC

The PA83 gene was chemically synthesized by GENEART AG (Regensburg, Germany) with a codon usage optimized for expression in humans. The adaptation of the codon usage included the removal of sequence elements, which could disturb viral and eukaryotic transcription and expression (e.g. six premature polyadenylation sites, premature stop signals for early transcription, RNA instability motifs and long G/C rich stretches.) The PA amino acid-sequence (735AA) of the recombinant MVA lacks the bacterial secretion signal (29 AA) and is 100% identical to the corresponding part of the translated pagA amino acid-sequence, thus making it identical to AA 30-764 of the sequence deposited under NCBI accession number AAF86457.1. For secretion of the PA protein in mammalian cells, a 21 AA amino-terminal secretion sequence (SecTag2; Ig kappa-chain leader sequence, from plasmid pSecTag2, Invitrogen) was N-terminally fused to the PA gene.

Similarly, instead of PA83, PA furin negative also can be used. Nucleotide 64-2277 of SEQ ID NO: 1 corresponds to the PA furin negative sequence after codon optimization used in the example.

Tetanus Toxin C fragment from *Clostridium tetanii* was C-terminally fused to the PA gene. The amino acid sequence in NCBI accession number ACR19198.1 was used as the reference gene. The TTC gene in MVA was chemically synthesized by GENEART AG (Regensburg, Germany) with a codon usage optimized for expression in humans. It is 100% identical to the corresponding part of the translated TTC amino acid-sequence. Nucleotide 2281-3642 of SEQ ID NO: 1 corresponds to the TTC sequence after codon optimization.

For the insertion of SecTag2-PA83-TTC into the MVA-BN® genome, a suitable recombination plasmid that targets IGR148/149 of the MVA-BN® genome was constructed. CEF cells were infected with MVA-BN® and subsequently transfected with the appropriate recombination plasmid. During homologous recombination, the plasmid flanking sequences recombine with the homologous sequences of the insertion site in the MVA-BN® virus genome. Markers allowing selection were inserted as a fusion gene under the control of a strong synthetic poxvirus promoter (PrS) in order to allow selection for the recombinant MVA virus.

Example 3

Construction of MVA-PA+LF

An LF variant, a truncated Lethal Factor of *B. anthracis*, was used for the construction of recombination plasmid. SecTag2 was N-terminally fused to the LF34-583(ΔLF) sequence, an inactive form of the LF protein. Alternatively, other LF7, LF50, LFE687C or other variants such as shown in Table 2 can be used. The LF34-583 was chemically synthesized by GENEART AG (Regensburg, Germany) with a codon usage optimized for expression in humans. The LF34-583 gene lacks the bacterial secretion signal and is identical to NCBI accession number AAR88322.1. PrS-SecTag2-PA83 (as in Example 2) and PrS-SecTag-LF34-583, flanked by MVA DNA sequences adjacent to the IGR148/149 site, were inserted into a suitable recombination plasmid which additionally contains a loxP-flanked selection cassette. Primary CEF cells were infected with MVA and subsequently transfected with the recombination plasmid. For excision of the selection cassette, expression plasmid encoding the Cre-recombinase was used.

Example 4

Construction of MVA-PA+LF+EF

The construction of MVA-PA+LF+EF was achieved by inserting a sequence encoding EF-K346R, an inactive form of EF, into the IGR 88/89 of the MVA-BN® genome of the construct of Example 3.

The EF-K346R sequence was chemically synthesized by GENEART AG (Regensburg, Germany) with a codon optimized expression in humans, using NCBI accession number AAA22374.1 as the reference sequence.

Further constructs can be generated in accordance with the above description.

Example 5

PA Expression in HeLa Cells

HeLa cells were infected (MOI=10) with the recombinant MVA-virus constructs expressing PA (MVA-mBN182) or PA-TTC (MVA-mBN181) and MVA-BN as wild type control. The infected cells were harvested and lysed 24 h post infection. The protein concentration of the cell lysates were quantified and equal amounts of total protein were loaded on a 4-12% SDS-polyacrylamide gel. After electrophoresis, the protein were blotted onto a PVDF membrane. After blocking the unspecific binding of proteins with 10% skim milk powder in TBS-T, the primary antibody, a mouse antibody directed against PA Abcam Ab1988 was used at a dilution of 1:1000 and the secondary antibody, Jackson anti-mouse IgG HRP, was used at 1:50000.

While the invention is described in further detail with regard to modified vaccinia virus Ankara, all the poxviruses mentioned in the description are also equally suited for use in the present invention.

Although the foregoing inventions have been described in detail by way of example for purposes of clarity of understanding, it will be apparent to a skilled person in the art that certain changes and modifications may be practiced within the scope of the claims.

The invention claimed is:

1. A recombinant poxvirus comprising a fusion protein coding sequence, the fusion protein comprising a tetanus toxin fragment C (TTC) and a *Bacillus anthracis* Protective antigen (PA) protein, wherein the coding sequence for the TTC encodes for amino acids 761-1213 of SEQ ID NO:2, and wherein the fusion protein enhances an immune response against *Bacillus anthracis* as compared with an immune response by a recombinant poxvirus comprising PA alone.

2. The recombinant poxvirus according to claim 1, wherein the TTC coding sequence comprises nucleotides 2281-3642 of SEQ ID NO: 1.

3. The recombinant poxvirus according to claim 1, wherein in the TTC is fused to the PA protein via a linker sequence.

4. The recombinant poxvirus of claim 1, wherein the poxvirus is a vaccinia virus.

5. The recombinant poxvirus of claim 4, wherein the vaccinia virus is a Modified Vaccinia Virus Ankara (MVA).

6. The recombinant poxvirus of claim 5, wherein the MVA is MVA-BN.

7. The recombinant poxvirus of claim 1, wherein the recombinant poxvirus further comprises a coding sequence for at least one *Bacillus anthracis* antigenic determinant selected from the group consisting of lethal factor (LF) and edema factor (EF).

8. The recombinant poxvirus according to claim 1, further comprising a nucleic acid encoding a co-stimulatory molecule.

9. The recombinant poxvirus of claim 8, wherein the co-stimulatory molecule is CD70, IL-12 and/or IL-15.

10. A vaccine or medicament for treating and/or preventing anthrax comprising the recombinant poxvirus of claim 6.

11. An isolated cell comprising the recombinant poxvirus according to claim 6.

12. A kit comprising the recombinant poxvirus according to claim 6 in a first vial or container for a first administration and in a second vial or container for a second administration.

13. A method for preventing or treating anthrax in a subject, the method comprising administering to the subject a recombinant poxvirus comprising a coding sequence for a fusion protein, the fusion protein comprising a tetanus toxin fragment C (TTC) and a *Bacillus anthracis* Protective antigen (PA) protein, wherein the coding sequence for the TTC encodes for amino acids 761-1213 of SEQ ID NO:2, and wherein said fusion protein enhances an immune response against *Bacillus anthracis* as compared with an immune response by a recombinant poxvirus comprising PA alone.

14. The method according to claim 13, wherein the TTC coding sequence comprises nucleotides 2281-3642 of SEQ ID NO: 1.

15. The method according to claim 13, wherein in the TTC is fused to the PA protein via a linker sequence.

16. The method of claim 13, wherein the poxvirus is a vaccinia virus.

17. The method of claim 16, wherein the vaccinia virus is a Modified Vaccinia Virus Ankara (MVA).

18. The method of claim 17, wherein the MVA is MVA-BN.

19. A method of generating a recombinant poxvirus comprising a coding sequence for a fusion protein, the fusion protein comprising a tetanus toxin fragment C (TTC) and a *Bacillus anthracis* Protective antigen (PA) protein, wherein the coding sequence for the TTC encodes for amino acids 761-1213 of SEQ ID NO:2, and wherein said fusion protein enhances an immune response against *Bacillus anthracis* as compared with an immune response by a recombinant poxvirus comprising PA alone the method comprising:
   a) infecting a host cell with a poxvirus;
   b) transfecting the infected cell with a recombinant vector comprising the fusion protein, said vector further comprising a genomic poxvirus sequence capable of directing the integration of the TTC and antigenic determinant coding sequences into the poxvirus genome; and
   c) identifying, isolating and, optionally, purifying the generated recombinant poxvirus.

* * * * *